(12) United States Patent
Sanders et al.

(10) Patent No.: US 9,414,991 B2
(45) Date of Patent: Aug. 16, 2016

(54) MEDICAL CONNECTOR HAVING LOCKING ENGAGEMENT

(71) Applicant: Becton Dickinson and Company Limited, Dun Laoghaire (IE)

(72) Inventors: Laurie Sanders, Glen Ridge, NJ (US); Jude Cancellieri, Oakland, NJ (US); Yan Yevmenenko, New York, NY (US)

(73) Assignee: Becton Dickinson and Company Limited, Dun Laoghaire (IE)

( * ) Notice: Subject to any disclaimer, the term of this patent is extended or adjusted under 35 U.S.C. 154(b) by 0 days.

(21) Appl. No.: 14/532,147

(22) Filed: Nov. 4, 2014

(65) Prior Publication Data

US 2015/0126958 A1 May 7, 2015

Related U.S. Application Data

(60) Provisional application No. 61/900,647, filed on Nov. 6, 2013.

(51) Int. Cl.
*A61J 1/18* (2006.01)
*A61J 1/20* (2006.01)
(Continued)

(52) U.S. Cl.
CPC ............ *A61J 1/2096* (2013.01); *A61J 1/18* (2013.01); *A61M 39/10* (2013.01); *A61M 39/1011* (2013.01); *A61M 39/14* (2013.01); *A61J 2001/2048* (2013.01); *A61M 2039/1016* (2013.01); *A61M 2039/1033* (2013.01); *A61M 2039/1066* (2013.01); *A61M 2039/1072* (2013.01)

(58) Field of Classification Search
CPC ..... A61J 1/18; A61J 1/2096; A61J 2001/2048; A61J 1/201; A61J 1/2055; A61M 2039/1016; A61M 2039/1033; A61M 39/1011; A61M 5/3271; A61M 5/3272; A61M 2005/3267; A61M 5/326; A61M 5/3202; A61M 5/3204; A61M 5/3257; A61M 2039/1072; A61M 2039/1066; A61M 2039/267; A61M 5/31578; A61M 5/3158; A61M 5/31581; A61M 2005/208; F16L 37/248; B43K 24/084
See application file for complete search history.

(56) References Cited

U.S. PATENT DOCUMENTS 2,344,739 A     3/1944   Shaff
2,622,561 A * 12/1952   Baker .................. B43K 24/086
                                                                             401/110

(Continued)

FOREIGN PATENT DOCUMENTS

EP         2462971 A1    6/2012
FR         2058576        5/1971
(Continued)

*Primary Examiner* — Adam Marcetich
(74) *Attorney, Agent, or Firm* — The Webb Law Firm

(57) ABSTRACT

A medical connector system including a first connector and a second connector. The first connector has a housing, a biasing member, and at least one projection. The second connector has at least one groove for receiving the at least one projection. The proximal end of the second connector is configured to be at least partially disposed within the distal end of the housing of the first connector. Upon application and release of a first set of opposing axial forces applied to the connector system, the first connector is locked to the second connector and, upon application and release of a second set of opposing axial forces, the first connector is released from the second connector. The connectors may include indicators to show when the connector system is in the locked position.

17 Claims, 32 Drawing Sheets

(51) Int. Cl.
A61M 39/14 (2006.01)
A61M 39/10 (2006.01)

(56) References Cited

U.S. PATENT DOCUMENTS

| | | | |
|---|---|---|---|
| 3,084,670 A * | 4/1963 | Dottlinger | B43K 24/086 401/111 |
| 3,084,671 A * | 4/1963 | Dottlinger | B43K 24/084 401/111 |
| 3,637,316 A * | 1/1972 | Bross | B43K 24/08 401/104 |
| 4,436,125 A | 3/1984 | Blenkush | |
| 4,564,054 A | 1/1986 | Gustavsson | |
| 4,673,404 A | 6/1987 | Gustavsson | |
| 4,932,937 A | 6/1990 | Gustavsson et al. | |
| 4,943,175 A * | 7/1990 | Heim | B43K 24/084 401/111 |
| 5,052,725 A | 10/1991 | Meyer et al. | |
| 5,104,158 A | 4/1992 | Meyer et al. | |
| 5,122,123 A * | 6/1992 | Vaillancourt | A61M 39/14 604/192 |
| 5,122,129 A | 6/1992 | Olson et al. | |
| 5,242,401 A * | 9/1993 | Colsky | A61M 5/326 604/110 |
| 5,280,876 A | 1/1994 | Atkins | |
| 5,290,254 A | 3/1994 | Vaillancourt | |
| 5,322,518 A | 6/1994 | Schneider et al. | |
| 5,334,188 A | 8/1994 | Inoue et al. | |
| 5,360,011 A | 11/1994 | McCallister | |
| 5,395,348 A | 3/1995 | Ryan | |
| 5,437,650 A | 8/1995 | Larkin et al. | |
| 5,464,123 A | 11/1995 | Scarrow | |
| 5,472,430 A | 12/1995 | Vaillancourt et al. | |
| 5,478,328 A | 12/1995 | Silverman et al. | |
| 5,487,728 A | 1/1996 | Vaillancourt | |
| 5,507,733 A | 4/1996 | Larkin et al. | |
| 5,509,911 A | 4/1996 | Cottone, Sr. et al. | |
| 5,545,152 A | 8/1996 | Funderburk et al. | |
| 5,607,392 A | 3/1997 | Kanner | |
| 5,609,584 A | 3/1997 | Gettig et al. | |
| 5,611,792 A | 3/1997 | Gustafsson | |
| 5,647,845 A | 7/1997 | Haber et al. | |
| 5,685,866 A | 11/1997 | Lopez | |
| 5,807,347 A | 9/1998 | Bonaldo | |
| 5,897,526 A | 4/1999 | Vaillancourt | |
| 6,063,068 A | 5/2000 | Fowles et al. | |
| 6,089,541 A | 7/2000 | Weinheimer et al. | |
| 6,113,583 A | 9/2000 | Fowles et al. | |
| 6,132,404 A | 10/2000 | Lopez | |
| 6,139,534 A | 10/2000 | Niedospial, Jr. et al. | |
| 6,221,041 B1 | 4/2001 | Russo | |
| 6,221,056 B1 | 4/2001 | Silverman | |
| 6,343,629 B1 | 2/2002 | Wessman et al. | |
| 6,358,236 B1 | 3/2002 | DeFoggi et al. | |
| 6,409,708 B1 | 6/2002 | Wessman | |
| 6,474,375 B2 | 11/2002 | Spero et al. | |
| 6,478,788 B1 | 11/2002 | Aneas | |
| 6,544,246 B1 | 4/2003 | Niedospial, Jr. | |
| 6,551,299 B2 | 4/2003 | Miyoshi et al. | |
| 6,585,695 B1 | 7/2003 | Adair et al. | |
| 6,599,273 B1 | 7/2003 | Lopez | |
| 6,610,040 B1 | 8/2003 | Fowles et al. | |
| 6,629,958 B1 | 10/2003 | Spinello | |
| 6,656,433 B2 | 12/2003 | Sasso | |
| 6,715,520 B2 | 4/2004 | Andreasson et al. | |
| 6,814,726 B1 | 11/2004 | Lauer | |
| 6,852,103 B2 | 2/2005 | Fowles et al. | |
| 6,875,203 B1 | 4/2005 | Fowles et al. | |
| 6,875,205 B2 | 4/2005 | Leinsing | |
| 6,911,025 B2 | 6/2005 | Miyahara | |
| 6,997,917 B2 | 2/2006 | Niedospial, Jr. et al. | |
| 7,040,598 B2 | 5/2006 | Raybuck | |
| 7,083,605 B2 | 8/2006 | Miyahara | |
| 7,097,209 B2 | 8/2006 | Unger et al. | |
| 7,261,707 B2 | 8/2007 | Frezza et al. | |
| 7,306,584 B2 | 12/2007 | Wessman et al. | |
| 7,326,194 B2 | 2/2008 | Zinger et al. | |
| 7,350,535 B2 | 4/2008 | Liepold et al. | |
| 7,354,427 B2 | 4/2008 | Fangrow | |
| 7,452,349 B2 | 11/2008 | Miyahara | |
| 7,547,300 B2 | 6/2009 | Fangrow | |
| 7,628,772 B2 | 12/2009 | McConnell et al. | |
| 7,648,491 B2 | 1/2010 | Rogers | |
| 7,658,734 B2 | 2/2010 | Adair et al. | |
| 7,743,799 B2 | 6/2010 | Mosler et al. | |
| 7,744,581 B2 | 6/2010 | Wallen et al. | |
| 7,758,560 B2 | 7/2010 | Connell et al. | |
| 7,803,140 B2 | 9/2010 | Fangrow, Jr. | |
| 7,867,215 B2 | 1/2011 | Akerlund et al. | |
| 7,879,018 B2 | 2/2011 | Zinger et al. | |
| 7,900,659 B2 | 3/2011 | Whitley et al. | |
| 7,927,316 B2 | 4/2011 | Proulx et al. | |
| 7,942,860 B2 | 5/2011 | Horppu | |
| 7,975,733 B2 | 7/2011 | Horppu et al. | |
| 8,096,525 B2 | 1/2012 | Ryan | |
| 8,122,923 B2 | 2/2012 | Kraus et al. | |
| 8,123,738 B2 | 2/2012 | Vaillancourt | |
| 8,137,332 B2 | 3/2012 | Pipelka | |
| 8,167,863 B2 | 5/2012 | Yow | |
| 8,177,768 B2 | 5/2012 | Leinsing | |
| 8,196,614 B2 | 6/2012 | Kriheli | |
| 8,206,367 B2 | 6/2012 | Warren et al. | |
| 8,211,069 B2 | 7/2012 | Fangrow, Jr. | |
| 8,226,628 B2 | 7/2012 | Muramatsu et al. | |
| 8,257,286 B2 | 9/2012 | Meyer et al. | |
| 8,267,127 B2 | 9/2012 | Kriheli | |
| 8,277,424 B2 | 10/2012 | Pan | |
| 8,317,741 B2 | 11/2012 | Kraushaar | |
| 8,317,743 B2 | 11/2012 | Denenburg | |
| 8,398,607 B2 | 3/2013 | Fangrow, Jr. | |
| 8,403,905 B2 | 3/2013 | Yow | |
| 8,425,487 B2 | 4/2013 | Beiriger et al. | |
| 8,449,521 B2 | 5/2013 | Thorne, Jr. et al. | |
| 8,454,579 B2 | 6/2013 | Fangrow, Jr. | |
| 2001/0042850 A1 * | 11/2001 | Cote, Sr. | A61M 39/02 251/149.1 |
| 2003/0070726 A1 | 4/2003 | Andreasson et al. | |
| 2003/0085574 A1 * | 5/2003 | Froment | F16L 37/084 285/376 |
| 2004/0111064 A1 * | 6/2004 | Asbaghi | A61M 5/3272 604/198 |
| 2004/0230158 A1 * | 11/2004 | Malenchek | A61M 5/3272 604/110 |
| 2005/0065495 A1 | 3/2005 | Zambaux | |
| 2005/0182383 A1 | 8/2005 | Wallen | |
| 2005/0215976 A1 | 9/2005 | Wallen | |
| 2005/0267400 A1 * | 12/2005 | Haarala | A61M 1/3653 604/43 |
| 2006/0189961 A1 * | 8/2006 | Miyahara | A61M 39/14 604/535 |
| 2007/0079894 A1 | 4/2007 | Kraus et al. | |
| 2008/0045919 A1 | 2/2008 | Jakob et al. | |
| 2008/0097371 A1 * | 4/2008 | Shemesh | A61J 1/2096 604/414 |
| 2008/0287914 A1 | 11/2008 | Wyatt et al. | |
| 2009/0069783 A1 | 3/2009 | Ellstrom et al. | |
| 2009/0159485 A1 | 6/2009 | Jakob et al. | |
| 2010/0179506 A1 | 7/2010 | Shemesh et al. | |
| 2010/0217226 A1 | 8/2010 | Shemesh | |
| 2011/0004183 A1 | 1/2011 | Carrez et al. | |
| 2011/0062703 A1 | 3/2011 | Lopez et al. | |
| 2011/0074148 A1 | 3/2011 | Imai | |
| 2011/0106046 A1 | 5/2011 | Hiranuma et al. | |
| 2011/0257621 A1 | 10/2011 | Fangrow | |
| 2011/0291406 A1 | 12/2011 | Kraft et al. | |
| 2012/0035580 A1 | 2/2012 | Fangrow | |
| 2012/0046636 A1 | 2/2012 | Kriheli | |
| 2012/0123381 A1 | 5/2012 | Kraus et al. | |
| 2012/0192968 A1 | 8/2012 | Bonnal et al. | |
| 2012/0192976 A1 | 8/2012 | Rahimy et al. | |
| 2012/0203193 A1 | 8/2012 | Rogers | |
| 2012/0265163 A1 | 10/2012 | Cheng et al. | |
| 2012/0279884 A1 | 11/2012 | Tennican et al. | |
| 2012/0316536 A1 | 12/2012 | Carrez et al. | |

(56) References Cited

U.S. PATENT DOCUMENTS

| | | |
|---|---|---|
| 2013/0006211 A1 | 1/2013 | Takemoto |
| 2013/0012908 A1 | 1/2013 | Yeung |
| 2013/0046246 A1* | 2/2013 | Cross ............... A61M 5/326 604/189 |
| 2013/0066293 A1 | 3/2013 | Garfield et al. |
| 2013/0072893 A1 | 3/2013 | Takemoto |
| 2013/0076019 A1 | 3/2013 | Takemoto |
| 2013/0079744 A1 | 3/2013 | Okiyama et al. |
| 2013/0160880 A1* | 6/2013 | Tiberghien ............ F16L 31/00 137/798 |
| 2013/0172818 A1* | 7/2013 | Schraga ............. A61M 5/3213 604/110 |
| 2013/0237932 A1* | 9/2013 | Thueer ............... A61M 5/2448 604/272 |
| 2013/0245563 A1* | 9/2013 | Mercer ............... A61M 5/3294 604/191 |
| 2014/0058333 A1* | 2/2014 | Cross ............... A61M 5/002 604/198 |
| 2014/0236100 A1* | 8/2014 | Ward ............... A61M 5/326 604/263 |

FOREIGN PATENT DOCUMENTS

| | | |
|---|---|---|
| WO | 2005011781 A1 | 2/2005 |
| WO | 2006103074 A1 | 10/2006 |
| WO | 2009024807 A1 | 2/2009 |
| WO | 2009090627 A1 | 7/2009 |
| WO | 2011050333 A1 | 4/2011 |
| WO | 2012069401 A1 | 5/2012 |
| WO | 2012119225 A1 | 9/2012 |
| WO | 2012168235 A1 | 12/2012 |
| WO | 2013025946 A1 | 2/2013 |
| WO | 2013054323 A1 | 4/2013 |
| WO | 2013066779 A1 | 5/2013 |
| WO | 2013115730 A1 | 8/2013 |
| WO | 2013179596 A1 | 12/2013 |

* cited by examiner

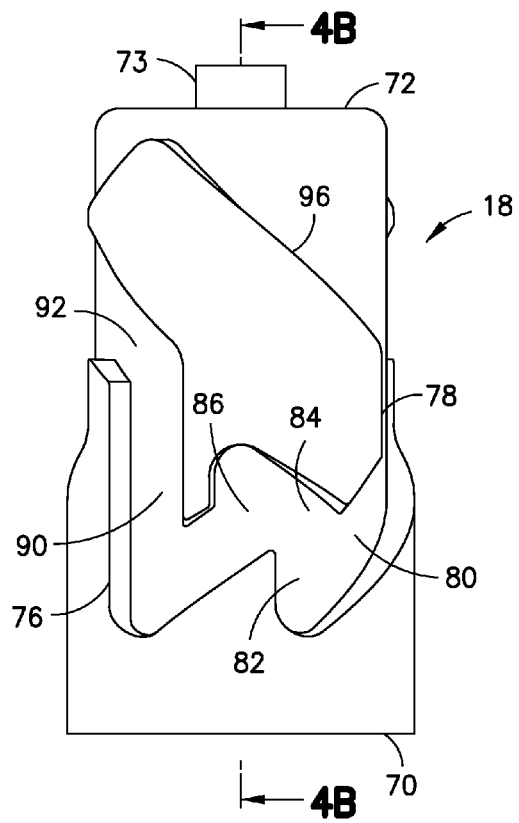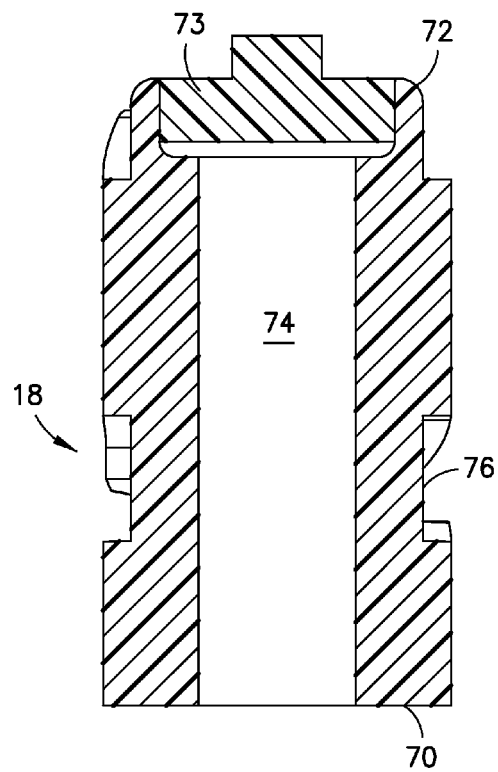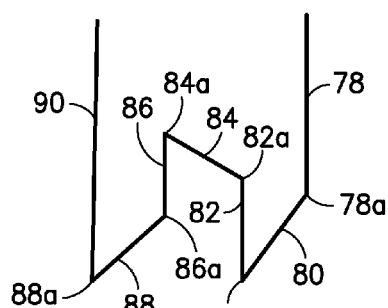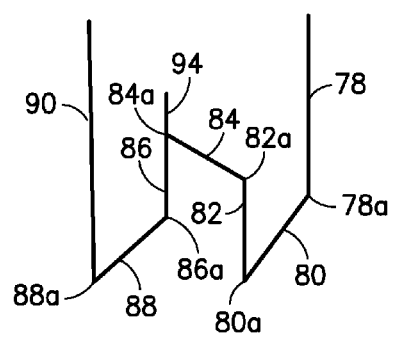
FIG.4A
FIG.4B
FIG.4C
FIG.4D

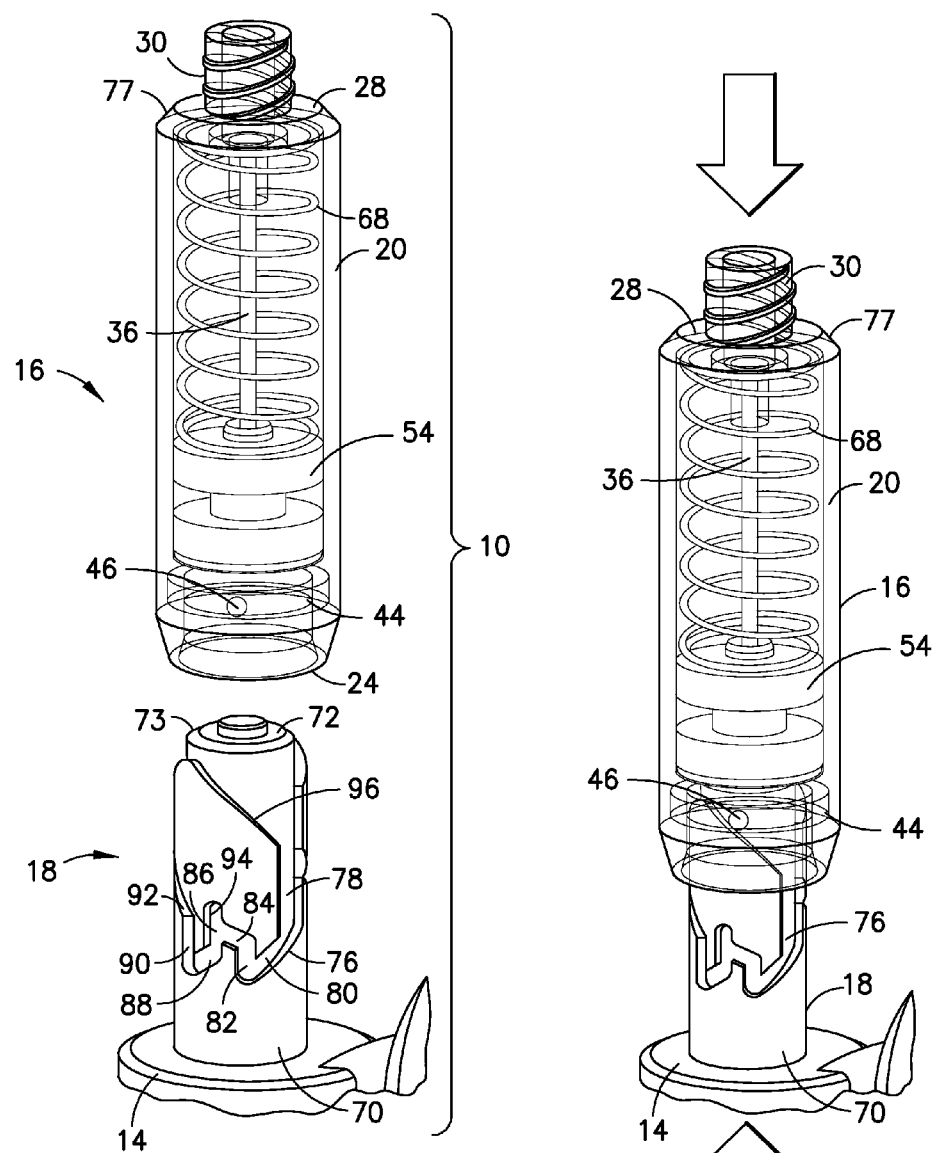

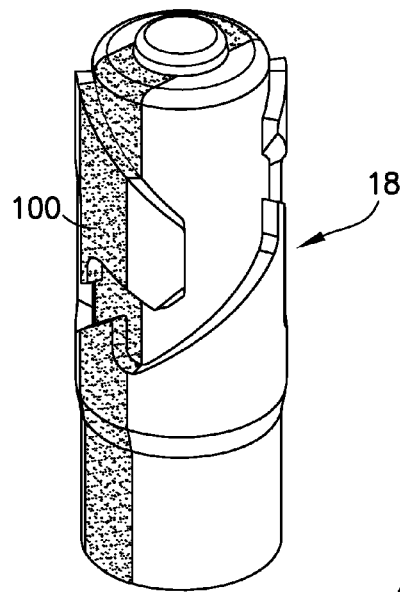
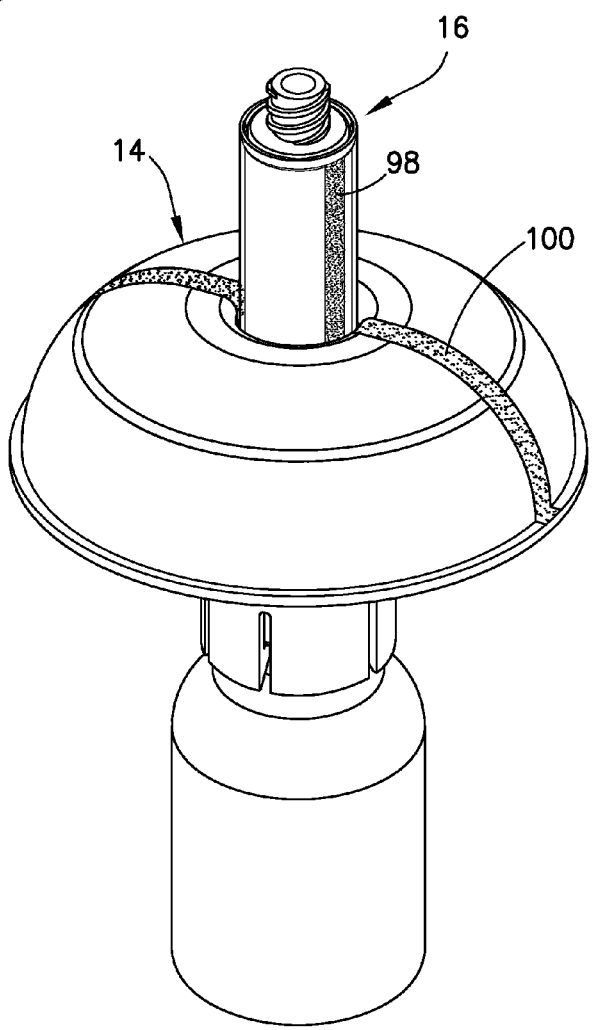
FIG.11
FIG.12

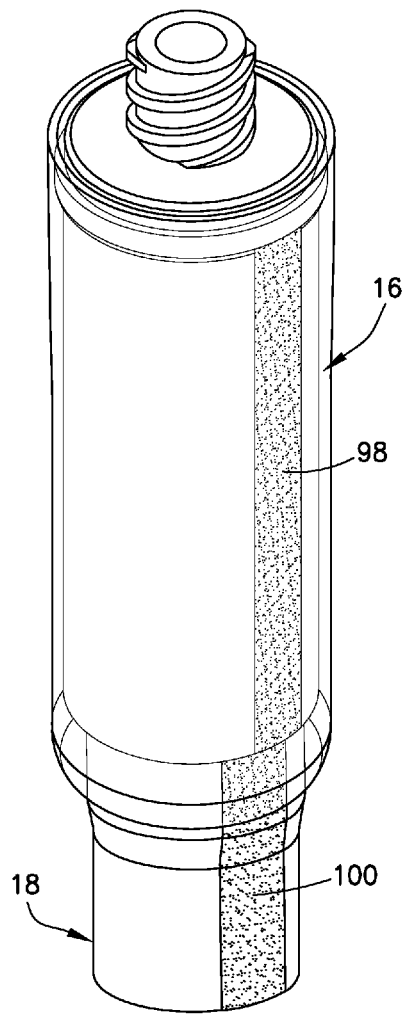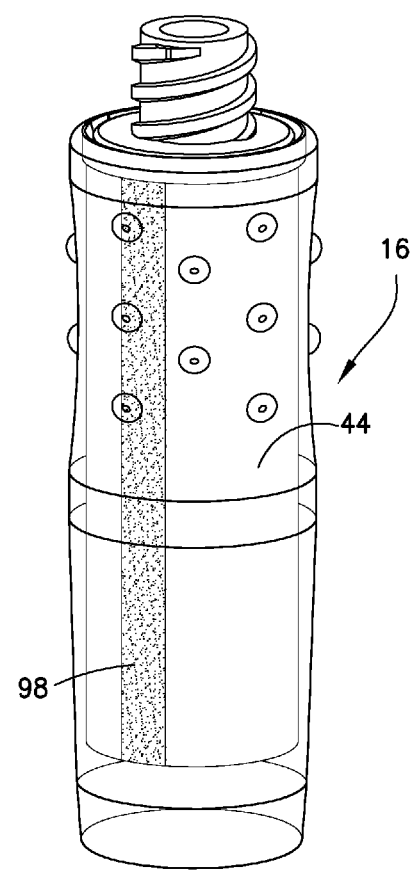
FIG.14
FIG.15

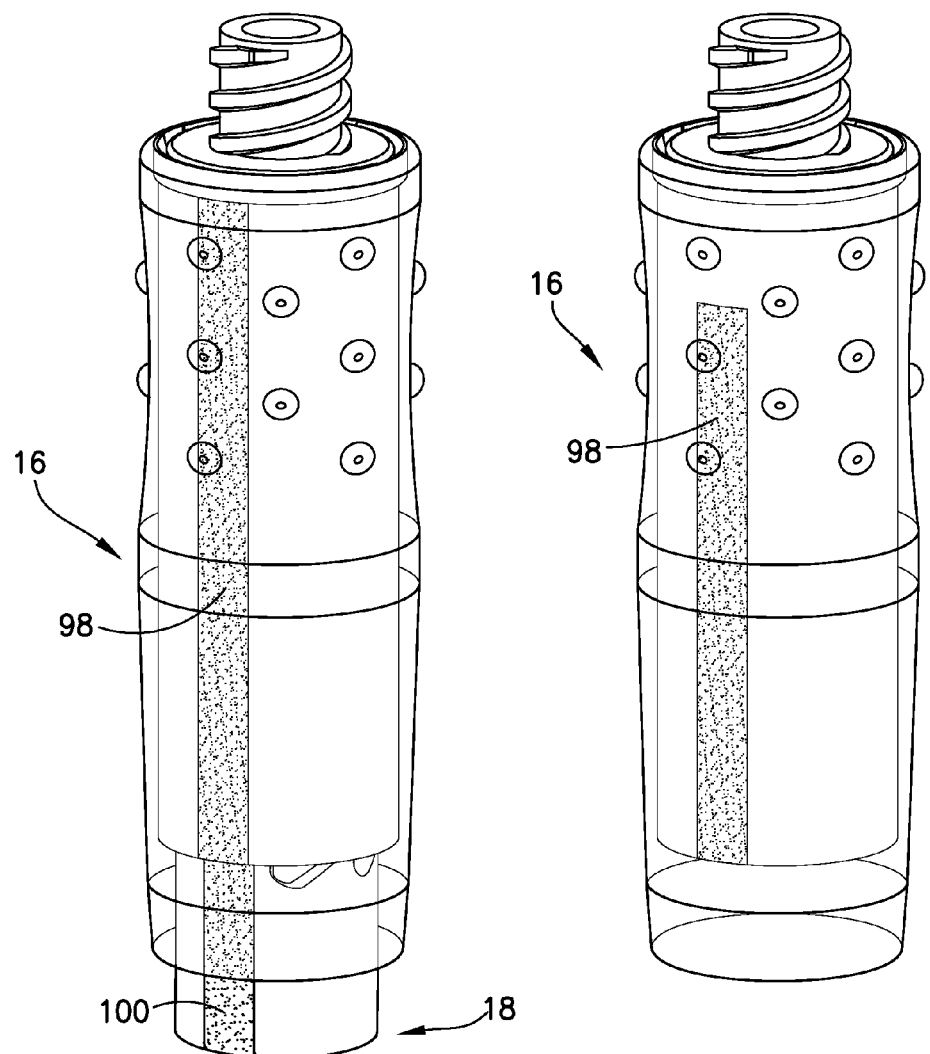

MEDICAL CONNECTOR HAVING LOCKING ENGAGEMENT

CROSS-REFERENCE TO RELATED APPLICATION

This application claims priority to U.S. Provisional Application Ser. No. 61/900,647, filed Nov. 6, 2013, which is hereby incorporated by reference in its entirety.

BACKGROUND OF THE INVENTION

1. Field of the Invention

The present invention relates to a connector system for a medical device. More specifically, the present invention relates to a connector system for enabling fluid transfer between a first medical device for receiving and/or dispensing fluids and a second medical device for receiving and/or dispensing fluids.

2. Description of Related Art

A problem in connection with drug preparation, drug administration, and other similar handling is the risk that medical and pharmacological staff are exposed to drugs or solvents which might escape into the ambient air. This problem is particularly serious when cytotoxins, antiviral drugs, antibiotics, and radiopharmaceuticals are concerned. Other hazardous areas may be sample taking, such as samples concerning virus infections or the like. When performing infusions, it is often necessary to inject a drug or other medical substance into the infusion fluid inside an infusion bag or other infusion fluid container. This is often done by means of penetrating a septum or other fluid barrier of an injection port on the infusion bag or on the infusion fluid line with a needle of a syringe filled with the medical fluid in question. However, even before this it may be necessary to transfer the medical fluid from a vial to a syringe and then from the syringe to a secondary container. In each of these steps, staff may be exposed to the medical fluid by means of contamination. Such contamination may be vaporized medical fluid or aerosol in the air. The contaminations may contaminate the staff through their lungs or vaporized medical fluid or aerosol in the air which condensates on the skin to thereafter penetrate the skin of the staff. Some medicaments are even known to penetrate protection gloves and thereby contaminate the staff.

Exposure to contaminations like this may, on a long term basis, give rise to alarmingly high concentrations of medicaments in the blood or the human body of the staff described above. It has been understood that due to the many transferring steps between e.g. vials, syringes, infusion systems etc., the risk for contamination during the actual insertion and retraction of a needle from the container, e.g. a vial, needs to be contained. Closed system transfer devices have been developed to ensure that the medicament is contained the transfer device during transfer of the medicament.

SUMMARY OF THE INVENTION

In one aspect, a medical connector system includes: a first connector having a proximal end and a distal end and including a housing, a biasing member, and at least one projection and a second connector having a proximal end and a distal end and including at least one groove for receiving the at least one projection. The biasing member may be a spring. The proximal end of the second connector is configured to be at least partially disposed within distal end of the housing of the first connector. Upon application and release of a first set of opposing axial forces applied to the proximal end of the first connector and the distal end of the second connector, the first connector is locked to the second connector and, upon application and release of a second set of opposing axial forces to the proximal end of the first connector and the distal end of the second connector, the first connector is released from the second connector.

When the first connector is locked to the second connector, the at least one projection of the first connector engages the at least one groove of the second connector and, when the first connector is released from the second connector, the at least one projection of the first connector is released from engagement with the at least one groove of the second connector.

Upon application and release of the first set of opposing axial forces applied to the proximal end of the first connector and the distal end of the second connector, the biasing member biases the first connector in a proximal direction with respect to the second connector such that the at least one projection of the first connector engages the at least one groove of the second connector and locks the first connector onto the second connector.

Upon application and release of the second set of opposing axial forces to the proximal end of the first connector and the distal end of the second connector, the biasing member biases the first connector in a proximal direction with respect to the second connector releasing the engagement between the at least one projection of the first connector and the at least one groove of the second connector.

The at least one groove may include: a first section extending axially in the distal direction; a second section extending from the distal end of the first section and sloping in the distal direction away from the distal end of the first section; a third section extending axially in the proximal direction from the distal end of the second section; a fourth section extending from the proximal end of the third section and sloping in the proximal direction away from the proximal end of the third section; a fifth section extending axially in the distal direction from the proximal end of the fourth section; a sixth section extending from the distal end of the fifth section and sloping in the distal direction away from the distal end of the fifth section; a seventh section extending axially in the proximal direction from the distal end of the sixth section; and an eighth section extending from the proximal end of the seventh section and sloping in the proximal direction away from the proximal end of the seventh section.

Alternatively, the at least one groove may further include an additional section extending axially in a proximal direction from the proximal end of the fourth section and the fifth section extends from a distal end of the additional section.

The second connector may further include a distally sloping ledge on an exterior surface extending to a proximal end of the first section of the at least one groove.

The first connector is locked to the second connector when the at least one projection of the first connector is disposed within a proximal end of the fourth section of the at least one groove of the second connector or within the proximal end of the additional section of the at least one groove of the second connector.

Upon application of the first set of opposing axial forces to the proximal end of the first connector and the distal end of the second connector, the at least one projection travels through the first and second sections of the at least one groove of the second connector. Upon release of the first set of opposing axial forces, the biasing member biases the first connector in a proximal direction with respect to the second connector such that the at least one projection travels through the third and fourth sections of the at least one groove of the second connector and is disposed within the proximal end of the fourth section of the second connector.

Upon application of the second set of opposing axial forces to the proximal end of the first connector and the distal end of the second connector, the at least one projection travels through the fifth and sixth sections of the at least one groove of the second connector. Upon release of the second set of opposing axial forces, the biasing member biases the first connector in a proximal direction with respect to the second connector such that the at least one projection travels through the seventh and eighth sections of the at least one groove of the second connector releasing engagement between the at least one projection and the at least one groove of the second connector.

The first connector may also include a cam member having the at least one projection and the cam member may be rotatably attached to the housing.

The first connector may also include a carrier that is slidably attached to the housing and a needle cannula and the second connector may also include an axial central passageway that extends from the proximal end to the distal end of the second connector. The biasing member may be disposed between a proximal end of the housing and the carrier.

Upon application of the first set of opposing axial forces applied to the proximal end of the first connector and the distal end of the second connector, the carrier contacts the proximal end of the second connector and energy is stored in the biasing member. In addition, when the first connector is locked to the second connector, the needle cannula is received in the central passageway and the distal end of the needle cannula extends from the distal end of the second connector. When the first connector is released from the second connector, the distal end of the needle cannula is contained within the housing of the first connector.

The carrier of the first connector may also include at least one sealing member. When the first connector is locked to the second connector, the needle cannula extends through the sealing member and is received within the central passageway of the second connector and a seal is created between the proximal end of the second connector and the sealing member. The seal is created between the proximal end of the second connector and the sealing member due to a distally directed force provided by the biasing member on the carrier and a proximally directed force provided on the second connector by the projection of the first connector.

The first connector may also include an attachment portion at the proximal end for attaching the first connector to first medical device.

The first connector and the second connector may also include indicators to show the user when the medical connector system is in the locked position. Such indicators may include axial bands or a bullseye configuration having a dot and a circle.

The present invention is also directed to a method of transferring a fluid from a first medical device for receiving or dispensing fluids to a second medical device for receiving or dispensing fluids. A first connector having a proximal end and a distal end, wherein the proximal end is connected to the first medical device and the distal end is open is provided. The first connector includes a housing and a needle cannula. A second connector having a proximal end and a distal end, wherein the distal end is connected to the second medical device, is also provided. The second connector includes a central passageway extending from the proximal end to the distal end. The proximal end of the second connector is at least partially inserted into the open distal end of the first connector. A first set of opposing axial forces is applied to and released from the proximal end of the first connector and the distal end of the second connector. The first connector is locked to the second connector upon release of the first set of opposing axial forces and the needle cannula extends into the central passageway beyond the distal end of the second connector and into the second medical device. The fluid is then transferred from the first medical device to the second medical device through the needle cannula.

The method may further include a step of applying and releasing a second set of opposing axial forces to the proximal end of the first connector and the distal end of the second connector. The first connector is released from the locking engagement with the second connector and the needle cannula is disposed within the housing of the first connector upon release of the second set of opposing axial forces.

BRIEF DESCRIPTION OF THE DRAWING(S)

FIG. 4A is a perspective view of a second connector of the medical connector system shown in FIG. 1 according to one aspect of the present invention.

FIG. 4B is a cross-sectional view of the second connector of FIG. 4A along line A-A according to one aspect of the present invention.

FIG. 4C is a schematic of a groove of the second connector of FIG. 4A according to one aspect of the present invention.

FIG. 4D is a schematic of a groove of the second connector according to an alternative aspect of the present invention.

FIG. 7A is a partially transparent perspective view of a medical connector system according to a further aspect of the present invention.

FIG. 7B is a partially transparent perspective view of the medical connector system of FIG. 7A according to one aspect of the present invention, showing the system upon insertion of the second connector into the housing of the first connector.

FIG. 11 is a perspective view of a second connector of a medical connector system shown according to a further aspect of the present invention, showing the connector with an indicator band in conjunction with a patient connector.

FIG. 12 is a perspective view of a medical connector system according to one aspect of the present invention, showing the first connector of FIG. 8 locked with the second connector of FIG. 9.

FIG. 14 is a perspective view of a medical connector system according to one aspect of the present invention, showing the first connector of FIG. 8 locked with the second connector of FIG. 11.

FIG. 15 is a perspective view of a first connector of a medical connector system shown according to another aspect of the present invention, showing the connector with a transparent housing and indicator band.

FIG. 18 is a perspective view of a medical connector system according to one aspect of the present invention, showing the first connector of FIG. 15 locked with the second connector of FIG. 16.

FIG. 19 is a perspective view of a first connector of a medical connector system shown according to yet another aspect of the present invention, showing the connector with a transparent housing and indicator band.

DESCRIPTION OF THE INVENTION

Figure 1:
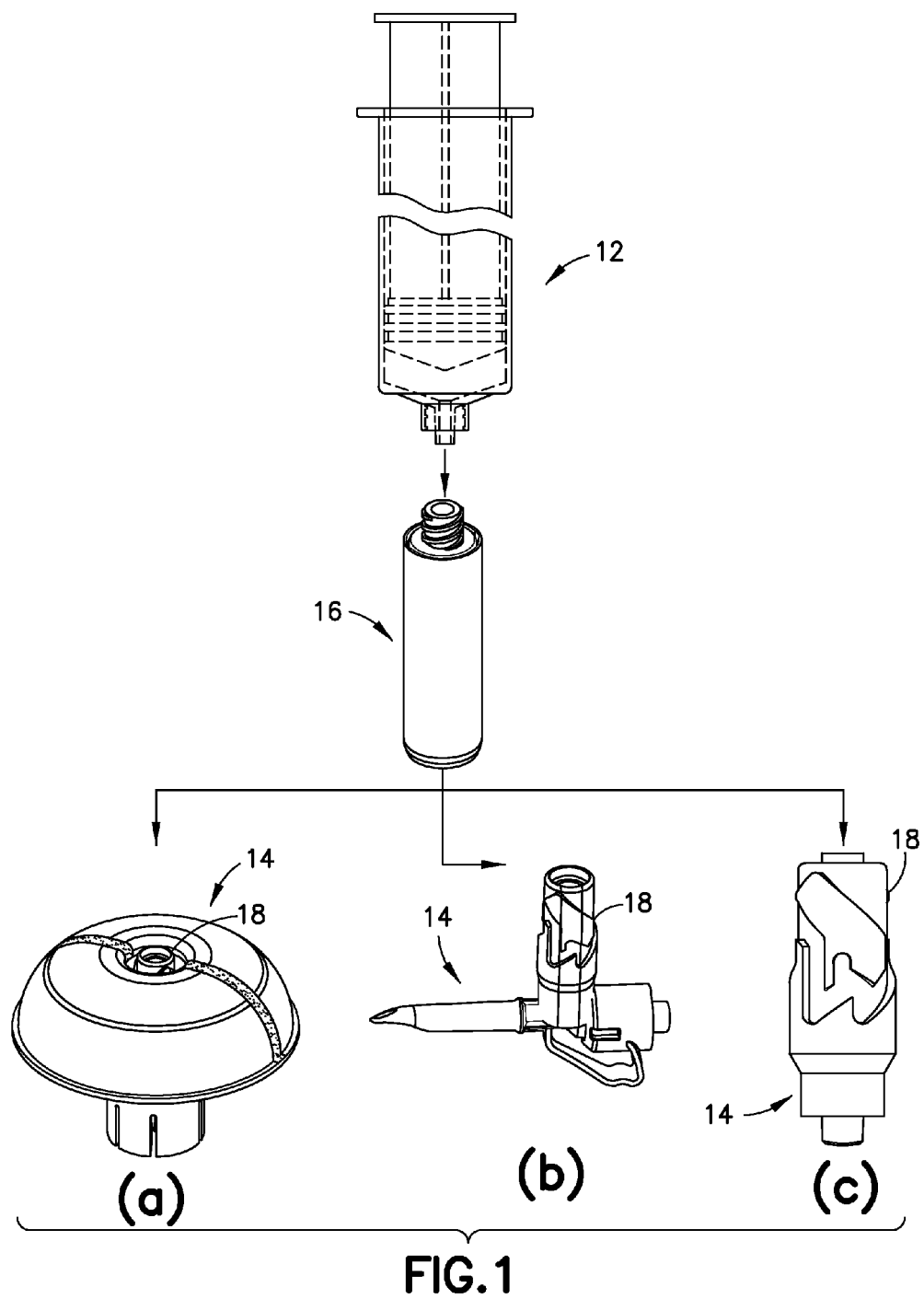
FIG. 1 is a perspective view of a medical connector system shown with a first medical device that is a syringe and a second medical device that is a pressure regulator (a), an IV bag adaptor (b), or a patient connector (c).

For purposes of the description hereinafter, the terms such as "end", "upper", "lower", "right", "left", "vertical", "horizontal", "top", "bottom", "lateral", "longitudinal" and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary aspects of the invention. Hence, specific dimensions and other physical characteristics related to the aspects disclosed herein are not to be considered as limiting. Further, it is to be understood that the invention may assume various alternative variations and step sequences, except where expressly specified to the contrary.

Figure 2:
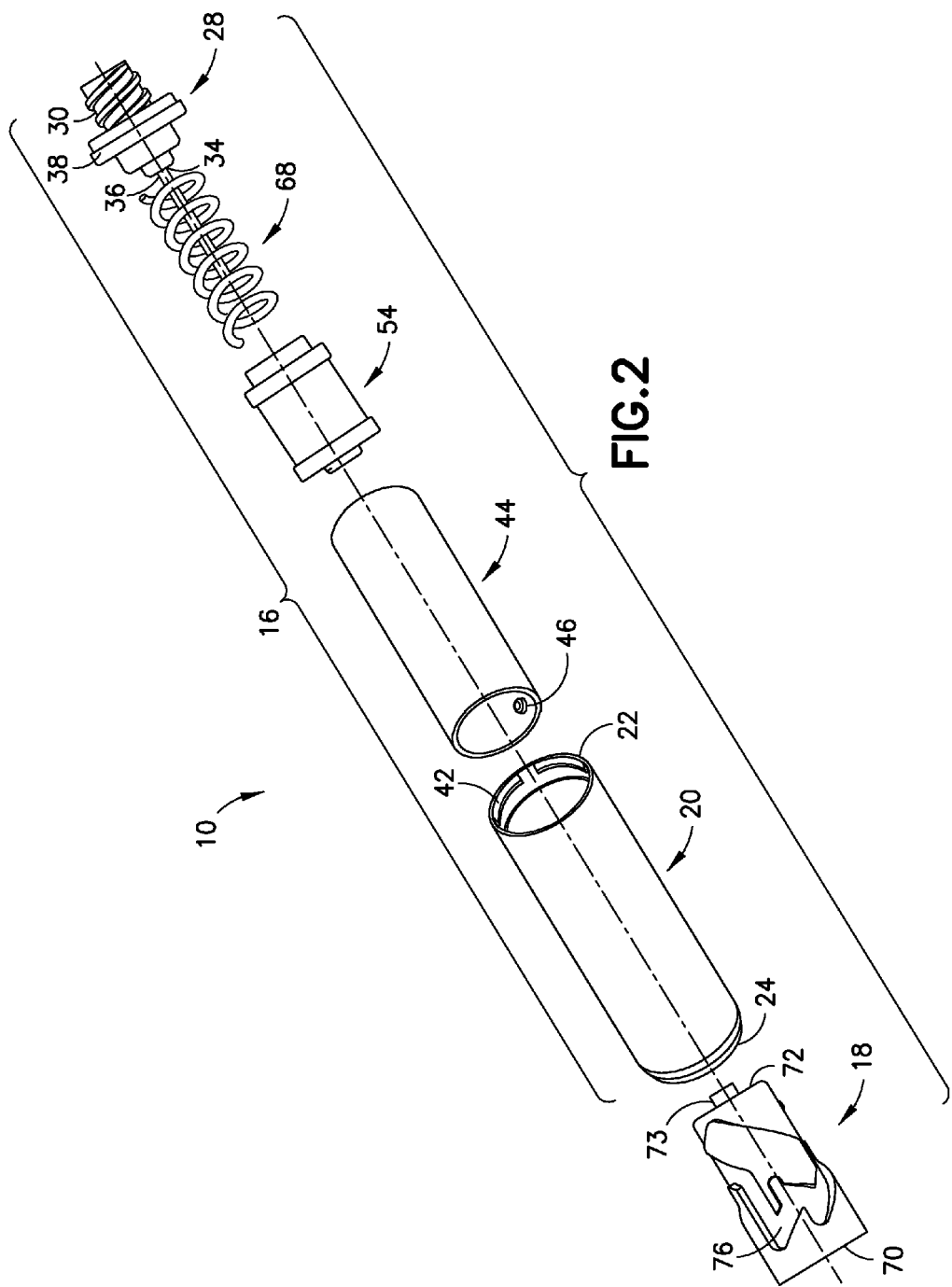
FIG. 2 is an exploded perspective view of the medical connector system shown in FIG. 1 according to one aspect of the present invention.

The present invention is directed to a connector system 10 for a medical device. In one aspect, the connector system 10 may be utilized for connecting and enabling fluid transfer between a first medical device 12 for receiving and/or dispensing fluids such as a syringe (FIG. 1) and a second medical device 14 for receiving and/or dispensing fluids such as a pressure equalization device (FIG. 1(a)), a vial adaptor, a patient connector (FIG. 1(b)), an IV bag adaptor (FIG. 1(c)), or a similar device used for receiving or dispensing fluids. The overall system is used to transfer a drug from an original container, such as a vial, to a patient. The medical connector 10 is the tool that is used to facilitate this closed system transfer. The medical connector system 10 includes a first connector 16 and a second connector 18. FIG. 2 shows an exploded view of one aspect of the medical connector system 10.

Figures 3A, 3B:
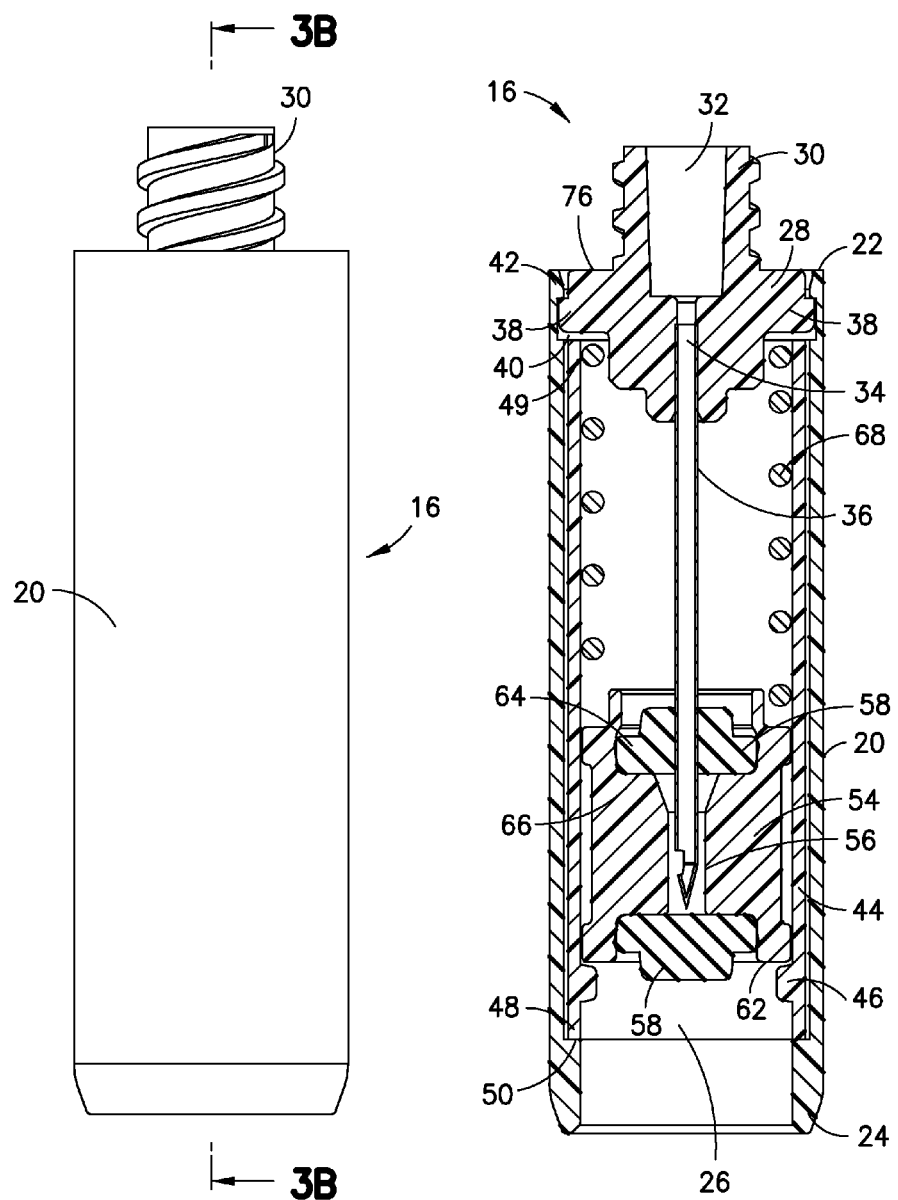
FIG. 3A is a perspective view of a first connector of the medical connector system shown in FIG. 1 according to one aspect of the present invention.
FIG. 3B is a cross-sectional view of the first connector of FIG. 3A along line A-A according to one aspect of the present invention, showing the first connector in an actuated position with the second connector omitted for clarity.

Referring to FIGS. 2-3B, the first connector 16 is embodied as a syringe adapter that is configured to receive a syringe or IV line at one end and mate with the second connector at the other end to facilitate the sealed transfer from a first container to a second container. The first connector 16, however, may be provided in connection with any other suitable medical devices. The first connector includes a housing 20 having a proximal end 22 and a distal end 24. The housing 20 has a generally cylindrical shape that defines a central opening 26.

A cap 28 is attached to the proximal end 22 of the housing 20. The cap 28 includes an attachment 30 to connect the first connector 16 to the first medical device 12. The attachment may be of any suitable configuration that allows the first connector 16 to be securely and sealing attached to the first medical device 12. Possible attachments include, but are not limited to, a luer connector or a snap-fit connector. The cap 28 has a central passageway 32 therethrough and a proximal end 34 of a needle cannula 36 is received in the central passageway 32 such that there is a fluid connection between the first medical device 12 and the needle cannula 36 allowing the fluid in the first medical device 12 to flow into the needle cannula 36.

In the aspect shown in FIGS. 2, 3A, 3B, and 6, the cap 28 is snap-fit onto the housing 20. A ledge 38 extends circumferentially around the perimeter of the cap 28 and is received in a corresponding circumferential recess 40 in the housing 20. At least one protrusion 42 having an upper surface that is sloped towards the distal end of the first connector 16 engages the upper surface of the ledge 38 and holds the cap 28 within the recess 40 of the housing 20. The sloped upper surface of the at least one protrusion 42 allows the cap 28 to be snap fit onto the housing 20 during assembly. Alternatively, any suitable means may be used to attach the cap 28 to the housing 20 as long at the cap 28 is securely attached to the housing 20. Possible alternative attachment means include, but are not limited to, alternative snap-fit configurations, welding in permanent connection, or a threaded connection. When the cap 28 is attached to the housing 20 the needle cannula 36 extends into the central opening 26 of the housing 20, but does not extend beyond the distal end 24 of the housing 20. The distal end of the housing 20 is open to allow at least a portion of the second connector 18 to be received within the central opening 26 as will be discussed in more detail below.

The first connector 16 also includes a cam member 44. The cam member 44 may be cylindrical in shape and includes at least one projection 46 extending into the central opening 26 of the housing 20 as shown in FIGS. 2, 3B, 6, 8A, and 8B. The cam member 44 is rotatably disposed within the housing 20. While the cam member 44 and the housing 20 are shown and described as cylindrical, they may take any suitable shape the allows for rotation of the cam member 44 in the housing 20, including but not limited to, a cone or a shape having an outer surface. The distal end 48 of the cam member 44 rests on a ledge 50 at the distal end 24 of the housing 20 and the proximal end of the cam member 44 is adjacent the cap 28 such that the cam member 44 is held within housing 20 by the ledge 50 and the cap 28.

Alternatively, as shown in FIGS. 7A-7G, 9A, and 9B, the cam member 44 may be ring shaped and may be held in a recess near the distal end 24 of the housing 20. The ring shaped cam member 44 may be disposed within the housing 20 as shown in FIGS. 7A-7G, 9A, and 9B or may be external to the housing 20 as shown in FIG. 8D, for example.

A carrier 54 is disposed within the central opening 26 of the housing 20. The carrier 54 has a generally cylindrical shape. The outermost surface of the carrier 54 is in sliding contact with either the inner surface of the cam member 44 if the cam member 44 has a cylindrical shape (FIGS. 2, 3B, 6, 8A, and 8B) or the inner surface of the housing 20 if the cam member 44 has a ring shape (FIGS. 7A-7G, 9A, and 9B) such that the carrier 54 may move in an axial direction within the housing 20. The carrier 54 includes an axial central opening 56 and at least one sealing member 58. The needle cannula 36 extends through both the axial central opening 56 of the carrier 54 and the at least one sealing member 58.

Figure 6:
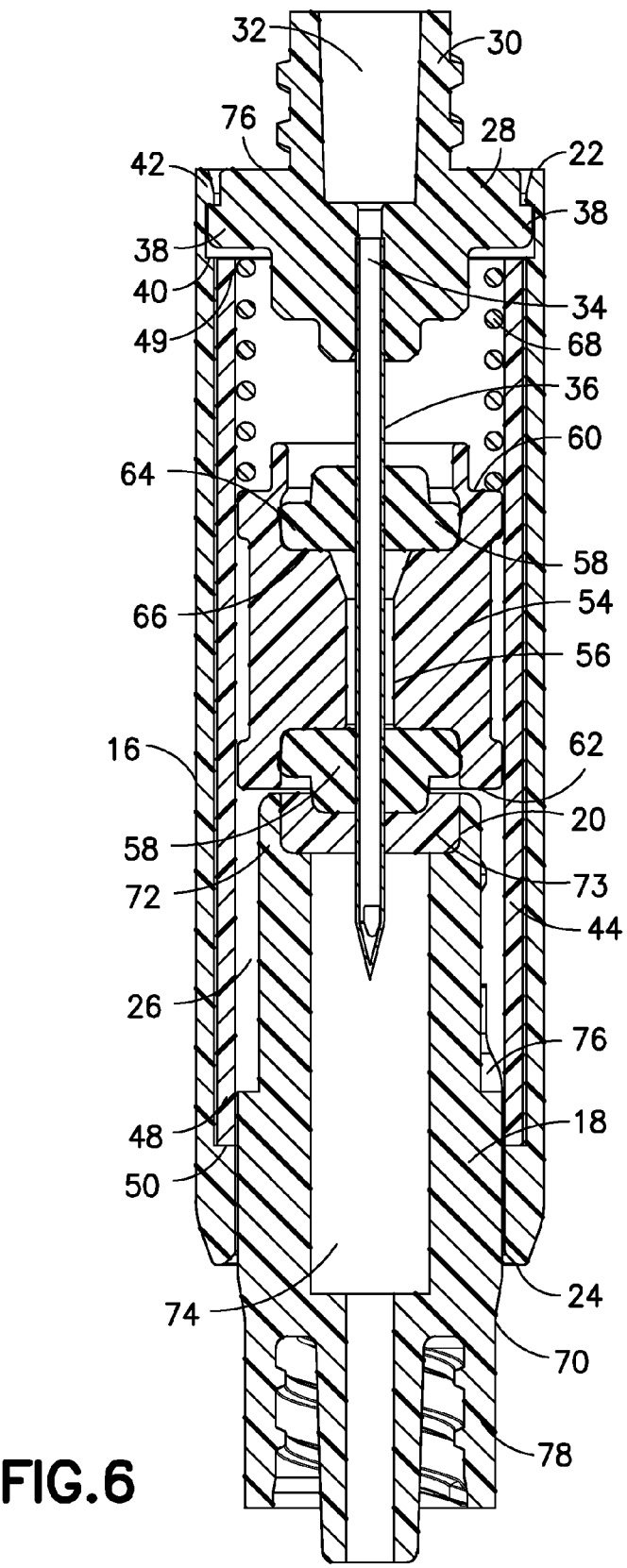
FIG. 6 is a cross-sectional view of the second connector of FIG. 5B according to one aspect of the present invention, showing the second connector inserted into but not locked to the first connector of FIG. 3A.

In the aspect shown in FIGS. 3A and 6, the two sealing members 58 are provided such that a first sealing member is at the proximal end 60 of the carrier 54 and a second sealing member is at the distal end 62 of the carrier 54. Preferably, at least one sealing member 58 is disposed at the distal end 62 of the carrier 54. A larger ledge portion of each sealing member 58 is received in a recess 66 in the carrier 54 to attach the sealing member 58 to the carrier 54. In an actuated or connected position, shown in FIG. 6, the carrier 54 is moved upward such that the needle cannula 36 extends through the carrier 54 and the sealing member(s) 58 to place the first medical device 12 in fluid communication with the second medical device 14. In a non-actuated, or unconnected position, as shown in FIG. 3B, the distal end of the needle cannula 36 will be positioned in the central opening 56 of the carrier 54 between the sealing members 58 to protect the sharpened end of the needle cannula 36 and contain any medicament that may be positioned within the lumen of the needle cannula 36. Alternatively, the needle cannula 36 could be contained in any structure that protects the sharpened end of the needle cannula 36 and contains any medicament that may be positioned within the lumen of the needle cannula 36, including, but not limited to, a single large membrane. The system 10 may also be utilized in connection with any other suitable drug delivery mechanism or arrangement.

A biasing member 68 is disposed between the cap 28 and the proximal end of the carrier 54. The biasing member 68 may be a spring, although other suitable biasing members may be utilized, including, but not limited to, a built in plastic spring or an elastic material such as rubber, TPE, or silicone. The elastic material could be placed in a grid format with multiple elastic strands or could be a single elastic strand. The biasing member 68 biases the carrier 54 towards the distal end 24 of the first connector 16 to ensure that the distal end of the needle cannula 36 is positioned within the carrier 54 when disconnected from the second connector 18 as described above.

The second connector 18 is generally cylindrical having a distal end 70 and a proximal end 72 and defining an axial central passageway 74, although other suitable shapes for the second connector 18 may be utilized. The distal end 70 of the second connector 18 may be integral with the second medical device 14 such as a pressure equalization device, a vial adaptor, a patient connector, an IV bag adaptor, or a similar fluid delivery device (FIGS. 4A, 4B, and 7A-9B) or may include an attachment for making a connection with such devices. For example, referring to FIGS. 5A, 5B, and 6, the second connector 18 is provided on a patient connector that includes an attachment 75 to connect the second connector 18 to a patient IV line or other suitable connection. The attachment 75 is shown as male locking luer connector, although other suitable attachment arrangements may be provided. The second connector 18 also includes a sealing member 73 at its proximal end 72.

The second connector 18 defines a groove 76 on its outer surface. The groove 76 has a zigzag shape extending in a number of directions (FIGS. 4A, 4C, 4D, and 5A). The groove 76 defines a first section 78 that extends substantially axially in a distal direction, i.e., extends generally toward the bottom end of the second connector 18. A second section 80 of the groove 76 extends from the distal end 78a of the first section 78 and slopes in a distal direction away from the distal end 78a of the first section 78, i.e., slopes downward and away from the bottom end of the first section 78. A third section 82 of the groove 76 extends substantially axially in a proximal direction from the distal end 80a of the second section 80, i.e., extends generally upward from the bottom end of the second section 80. A fourth section 84 of the groove 76 extends from the proximal end 82a of the third section 82 and slopes in a proximal direction away from proximal end 82a of the third section 82, i.e., slopes upward and away from the top end of the third section 82. A fifth section 86 of the groove 76 extends substantially axially in a distal direction from the proximal end 84a of the fourth section 84, i.e., extends downward from the top end of the fourth section 84. A sixth section 88 of the groove 76 extends from the distal end 86a of the fifth section 86 and slopes in a distal direction away from distal end 86a of the fifth section 86, i.e., slopes downward and away from the bottom end of the fifth section 86. A seventh section 90 of the groove 76 extends substantially axially in a proximal direction from the distal end 88a of the sixth section 88, i.e., extends upward from the bottom end of the sixth section 88. An eighth section 92 of the groove 76 extends from the proximal end of the seventh section 90 and slopes in a proximal direction away from proximal end of the seventh section 90, i.e., slopes upward and away from the top end of the seventh section 90.

The first 78, third 82, fifth 86, and seventh 90 sections of the groove 76 have been described as extending in a substantially axial direction which includes vertically or parallel to the longitudinal axis of the second connector 18 and in a slightly sloping direction as long as they are directed in a proximal direction or distal direction overall.

In an alternative aspect, as shown in FIGS. 4D and 7A-9B, an additional section 94 may extend axially in a proximal direction from the proximal end 84a of the fourth section 84 and fifth section 86 may extend from the distal end 84a of the additional section 94, i.e., the additional section 94 may extend from the top end of the fourth section 84 and the fifth section 86 may extend from the bottom end of the additional section 94. The additional section 94 helps to provide additional security in the locked position but is not required to form a locking connection.

A proximally sloping ledge 96, i.e., a ledge that slopes towards the bottom of the second connector 18, extends along the exterior of the second connector 18. The distal end of the sloping ledge 96 extends to the proximal end of the first section 78 of the groove 76, i.e., the bottom end of the sloping ledge 96 extends to the top end of the first section 78 of the groove 76.

Figures 5A, 5B:
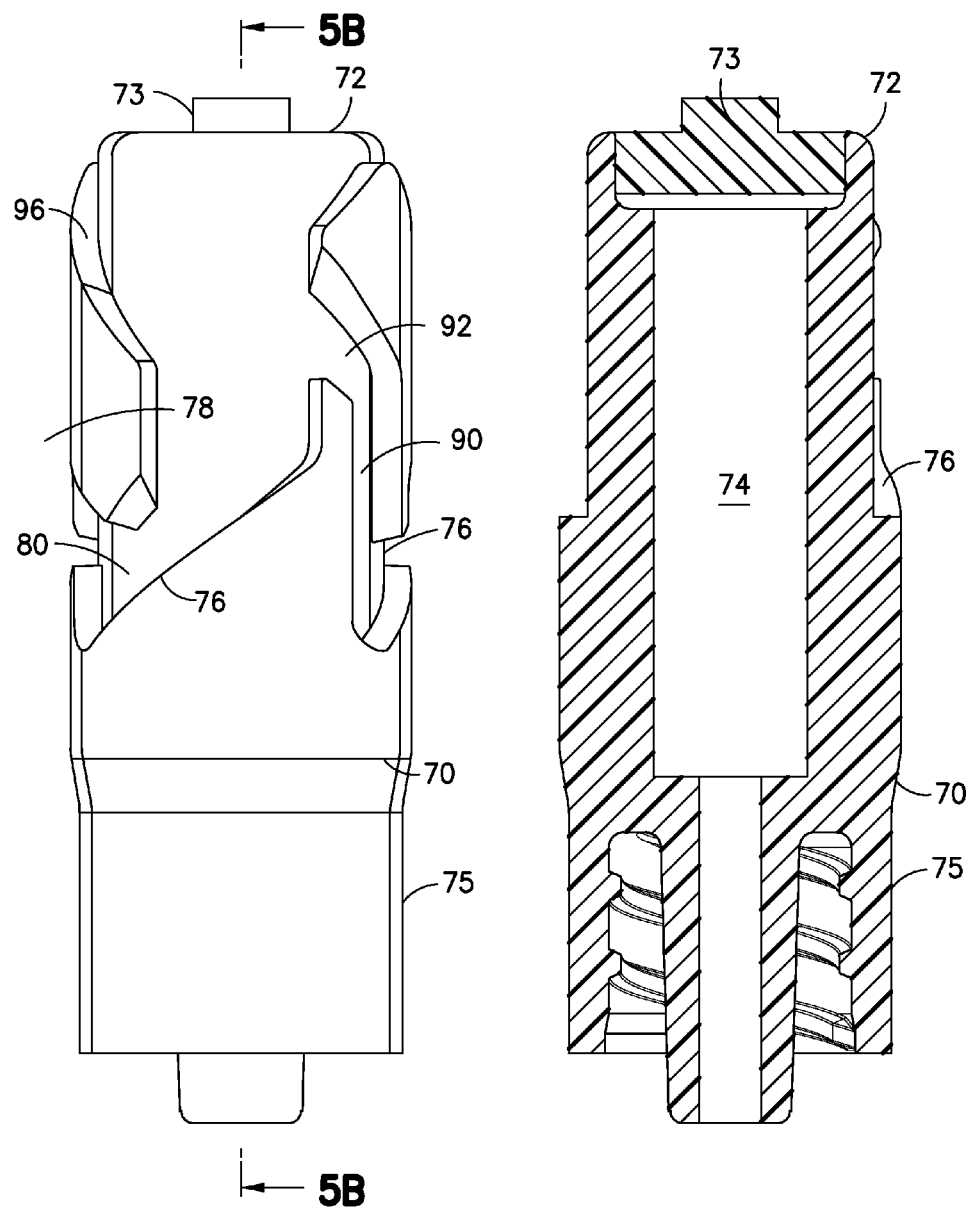
FIG. 5A is a perspective view of a patient connector provided with the second connector of the medical connector system of FIG. 1 according to one aspect of the present invention.
FIG. 5B is a cross-sectional view of the second connector of FIG. 5A along line A-A according to one aspect of the present application.

The first connector 16 may be provided with two projections 46 on opposite sides of the cam member 44 (FIG. 3B) and the second connector 18 may be provided with two grooves 76 on opposite sides of the second connector 18 (FIG. 5A).

Figure 7C:
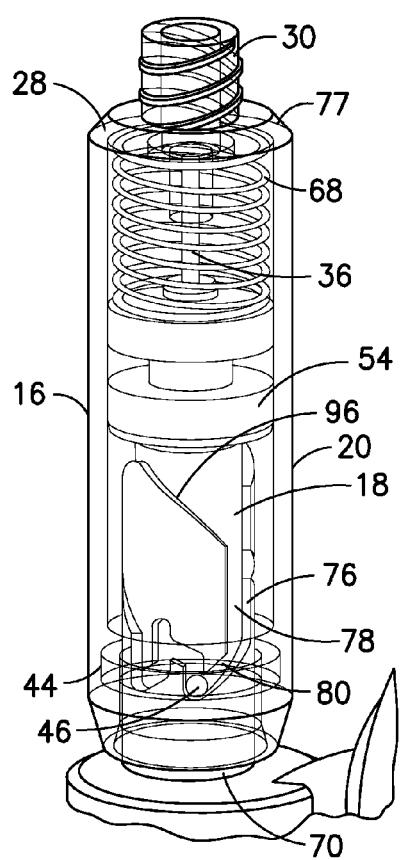
FIG. 7C is a partially transparent perspective view of the medical connector system of FIG. 7A according to one aspect of the present invention, showing the system after application of a first set of opposing forces applied to the first connector and the second connector.

In use, the proximal end 72 of the second connector 18 is inserted into the open distal end 24 of the housing 20 of the first connector 16 (FIG. 7B). The projection 46 on the cam member 44 of the first connector 16 either contacts the sloping ledge 96 on the second connector 18 or the projection 46 is received in the first section 78 of groove 76 depending on the orientation of the first connector 16 with respect to the second connector 18. The proximal end 72 of the second connector 18 contacts the distal end 62 of the carrier 54. The second connector 18 may include a sealing member 73 positioned adjacent to the proximal end 72 of the second connector 18 that engages and forms a seal with the sealing member 58 positioned at the distal end 62 of the carrier 54. After insertion, opposing axial forces are placed on the proximal end 77 of the first connector 16 and the distal end 70 of the second connector 18 (FIG. 7C). The carrier 54 is forced in a proximal direction with respect to the housing 20 by the proximal end 72 of the second connector 18. As a result, energy is stored in the biasing member 68. In the case of a spring, the energy is stored by compression of the spring. At the same time, the second connector 18 is further received in the central opening 26 of the housing 20 of the first connector 16. As the second connector 18 is further received in the central opening 26 of the housing 20 of the first connector 16, the projection 46 on the cam member 44, which is rotatably disposed in the housing 20 of the first connector 16, either follows the sloping ledge 96 of the second connector 18 to the groove 76 and proceeds through the first section 78 and second section 80 of the groove 76 or directly proceeds through the first section 78 and second section 80 of the groove 76.

Figure 7D:
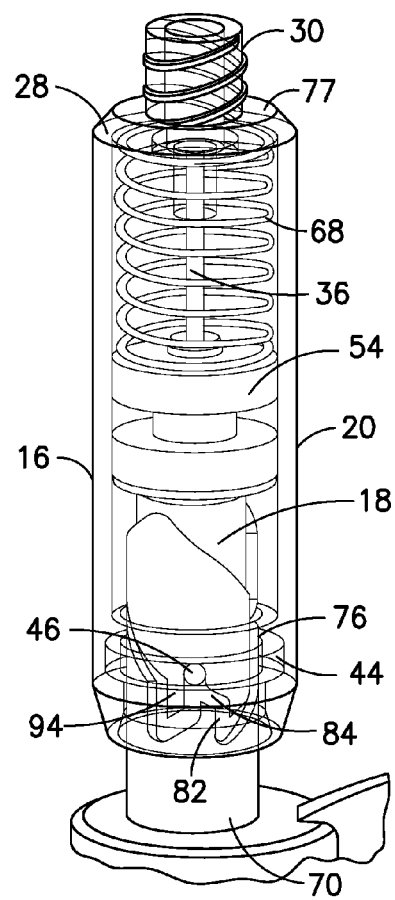
FIG. 7D is a transparent perspective view of the medical connector system of FIG. 7A according to one aspect of the present invention, showing the system in a locked state after release of the first set of opposing forces applied to the first connector and the second connector.

When the opposing axial forces are released, the energy stored in the biasing member 68 forces the housing 20 of the first connector 16 in a proximal direction with respect to the second connector 18 (FIG. 7D). As a result, the projection 46 on the cam member 44 proceeds through the third section 82 and fourth section 84 of the groove 76 and, if the additional section 94 is provided between the fourth section 84 and fifth section 86 of the groove 76 into the additional section 94. The proximal force provided by the biasing member 68 on the housing 20 and, thus, the projection 46 on the cam member 44 holds the projection 46 in the groove 76 such that the first connector 16 is now locked onto the second connector 18. In this locked state, the housing 20 can still be rotated with respect to the second connector 18 without disengaging the first connector 16 from the second connector 18.

Preferably, when the first connector 16 and the second connector 18 are in this locked engagement, the proximal end 72 of the second connector 18 is in sealing engagement with a sealing member 58 on the distal end 62 of the carrier 54. The distal force provided by the biasing member 68 on the carrier 54 and the proximal force provided on the second connector 18 by the projection 46 on the cam member 44 help to assure a good seal between the sealing member 58 and the proximal end 72 of the second connector 18.

When the first connector 16 and the second connector 18 are in this locked engagement, the needle cannula 36 extends into the axial central passageway 74 of the second connector 18 and into the second medical device 14. This provides a fluid path from the first medical device 12 through the needle cannula 36 into the second medical device 14.

Figures 7E, 7F:
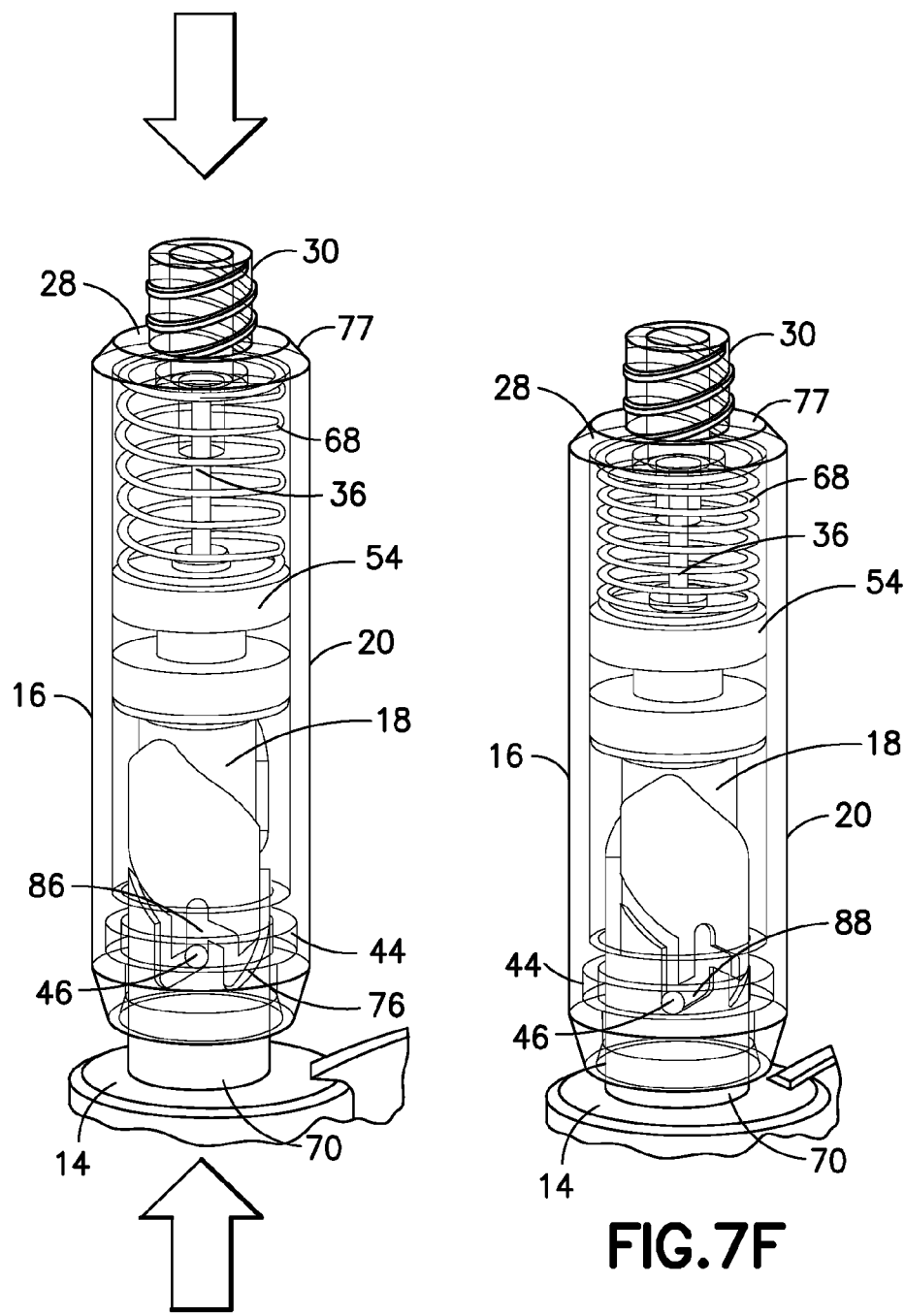
FIG. 7E is a transparent perspective view of the medical connector system of FIG. 7A according to one aspect of the present invention, showing the system at the beginning of the application of a second set of opposing forces applied to the first connector and the second connector.
FIG. 7F is a transparent perspective view of the medical connector system of FIG. 7A according to one aspect of the present invention, showing the system at the completion of the application of a second set of opposing forces applied to the first connector and the second connector.

When it is desired to release the locking connection between the first connector 16 and the second connector 18, opposing axial forces are again placed on the proximal end 77 of the first connector 16 and the distal end 70 of the second connector 18 (FIGS. 7E and 7F). The carrier 54 is forced in a proximal direction with respect to the housing 20 by the proximal end 72 of the second connector 18. As a result, energy is stored in the biasing member 68. In the case of a spring, the energy is stored by compression of the spring. At the same time, the second connector 18 is further received in the central opening 26 of the housing 20 of the first connector 16. As the second connector 18 is further received in the central opening 26 of the housing 20 of the first connector 16, the projection 46 on the cam member 44 proceeds through the fifth section 86 and sixth section 88 of the groove 76.

Figure 7G:
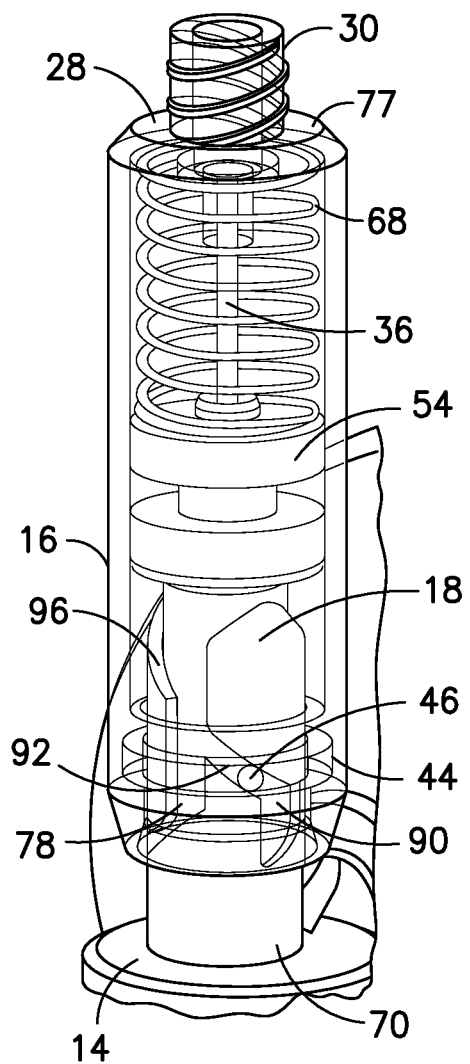
FIG. 7G is a transparent perspective view of the medical connector system of FIG. 7A according to one aspect of the present invention, showing the system in a released state after release of the second set of opposing forces applied to the first connector and the second connector.

When the opposing axial forces are released, the energy stored in the biasing member 68 forces the housing 20 of the first connector 16 in a proximal direction with respect to the second connector 18 (FIG. 7G). As a result of the proximal force on the housing 20, the projection 46 on the cam member 44 proceeds through the seventh section 90 and eighth section 92 of the groove 76 and the first connector 16 is released from engagement with the second connector 18. The distal end of the needle cannula 36 is once again contained in carrier 54 of the first connector 16.

In the released position the tip of the needle cannula 36 is contained in the axial central opening 56 of the carrier 54 between the two sealing members 58. Thus, not only is the user protected from an accidental needle stick, but any fluid that may remain in the needle cannula 36 is contained in the needle cannula 36 and or the carrier 54 by the sealing members 58.

While the connector system 10 has been described and shown as having a biasing member 68, another aspect does not include a biasing member. In this aspect, the user applies opposing axial forces on the proximal end 77 of the first connector 16 and the distal end 70 of the second connector 18 pushing the first connector 16 onto the second connector 18 until the protrusion 46 has traveled through the first 78 and second 80 sections of the groove 76 and the first connector 16 cannot be advanced on the second connector 18 any further. Then the user applies opposing axial forces on the proximal end 77 of the first connector 16 and the distal end 70 of the second connector 18 pulling the first connector 16 away from the second connector 18 until the protrusion 46 has traveled through the third 82 and fourth 84 sections of the groove 76 and into the additional section 94. The additional section 94 is in the form of detent to provide a locking engagement with the protrusion 46. When the protrusion 46 is locked in the additional section 94, the first connector 16 is locked to the second connector 18.

When it is desired to release the locking connection between the first connector 16 and the second connector 18, the user again applies opposing axial forces on the proximal end 77 of the first connector 16 and the distal end 70 of the second connector 18 pushing the first connector 16 onto the second connector 18 until the protrusion 46 is released from the additional section 94 and travels through the fifth 86 and sixth 88 sections of the groove 76 and the first connector 16 cannot be advanced on the second connector 18 any further. Then the user applies opposing axial forces on the proximal end 77 of the first connector 16 and the distal end 70 of the second connector 18 pulling the first connector 16 away from the second connector 18 until the protrusion 46 has traveled through the seventh 90 and eighth 92 sections of the groove 76 and the first connector 16 is released from the second connector 18.

As shown in FIGS. 8-25, the first connector 16 may have an indicator band 98 extending axially on the outer surface of the cam member 44. In this case, the housing 20 of the first connector 16 is transparent. The second connector 18 may have an indicator band 100 extending axially on its outer surface. The indicator bands 98, 100 are placed on the cam member 44 and the second connector 18 such that, when the first connector 16 is in locking engagement with the second connector 18, the indicator band 98 on the cam member 44 which will be visible through the transparent housing 20 will be aligned with the indicator band 100 on the second connector 18 to give a visual indication to the user that the connector system is locked. Preferably, the indicator band 98 on the cam member 44 is located 90° around the circumference of the cam member 44 from the protrusion 46. Alternatively, if the second connector 18 is integral with the second medical device 14, the indicator band 100 may be included on the exterior surface of the second medical device 14.

Figure 8:
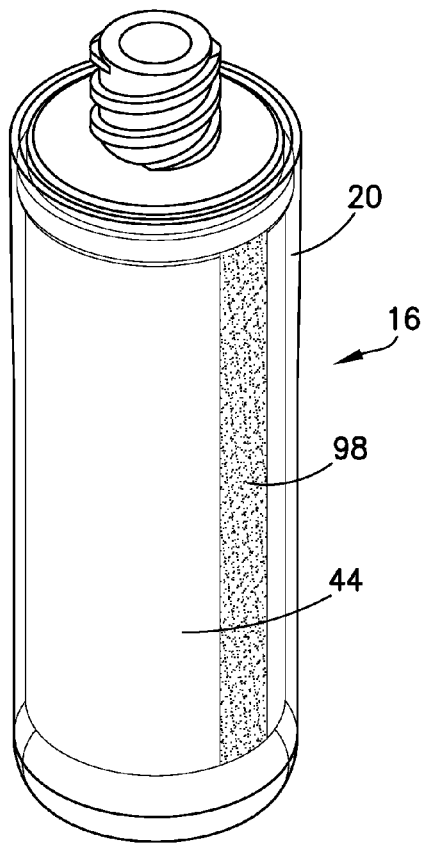
FIG. 8 is a perspective view of a first connector of a medical connector system shown according to a further aspect of the present invention, showing the connector with a transparent housing and indicator band.
Figure 9:
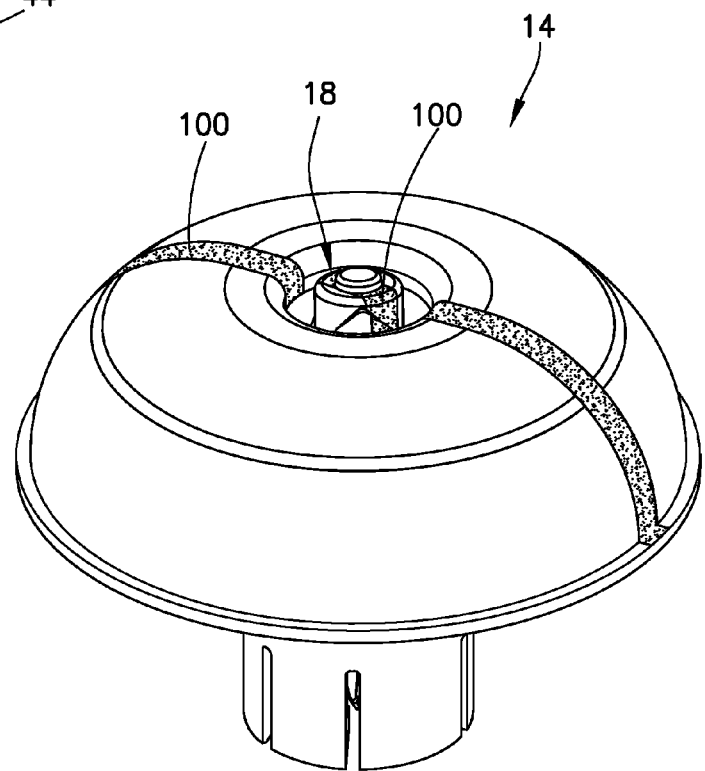
FIG. 9 is a perspective view of a second connector of a medical connector system shown according to a further aspect of the present invention, showing the connector with an indicator band in conjunction with a vial adapter.
Figure 10:
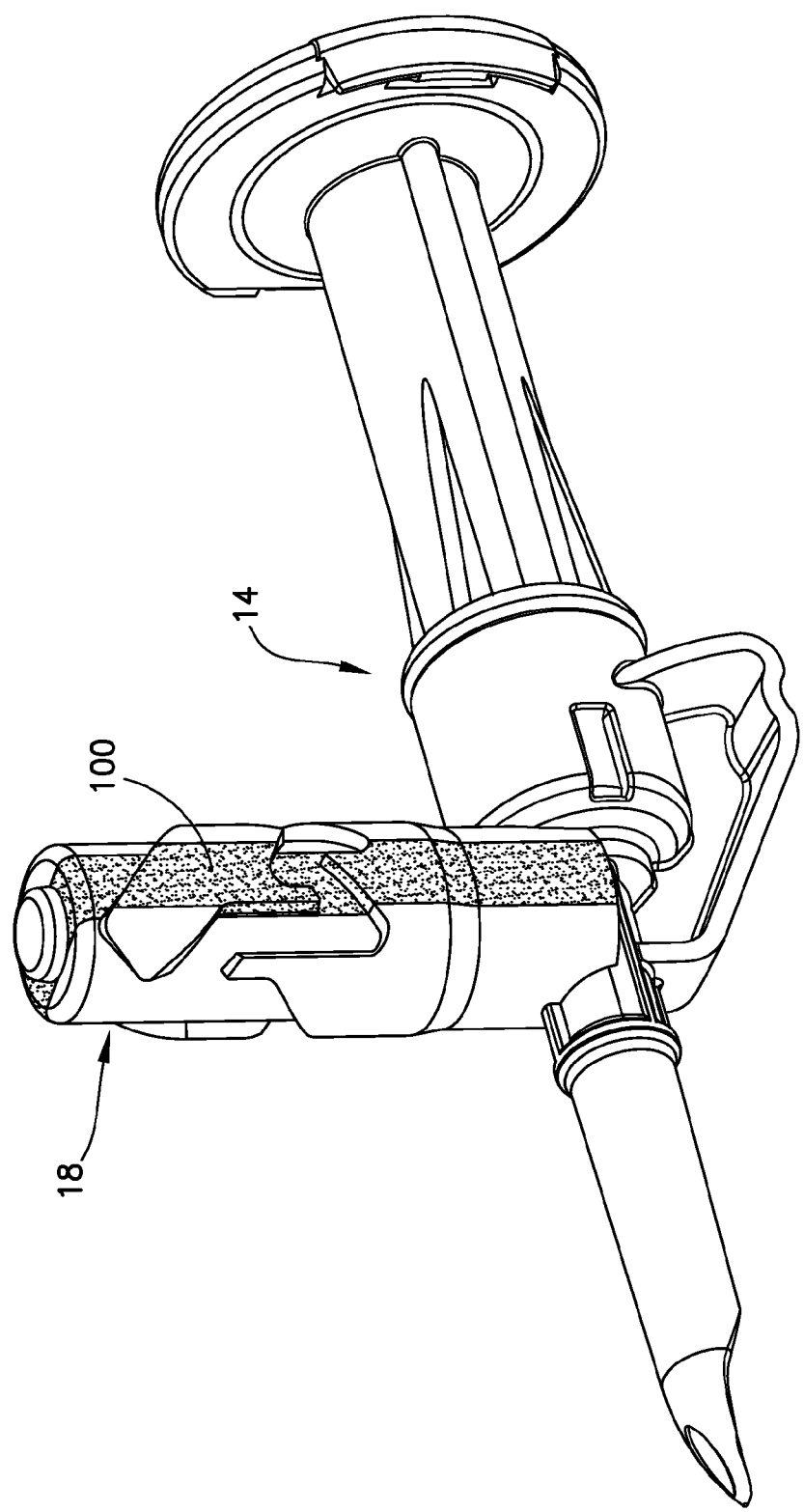
FIG. 10 is a perspective view of a second connector of a medical connector system shown according to a further aspect of the present invention, showing the connector with an indicator band in conjunction with an IV bag spike.
Figure 13:
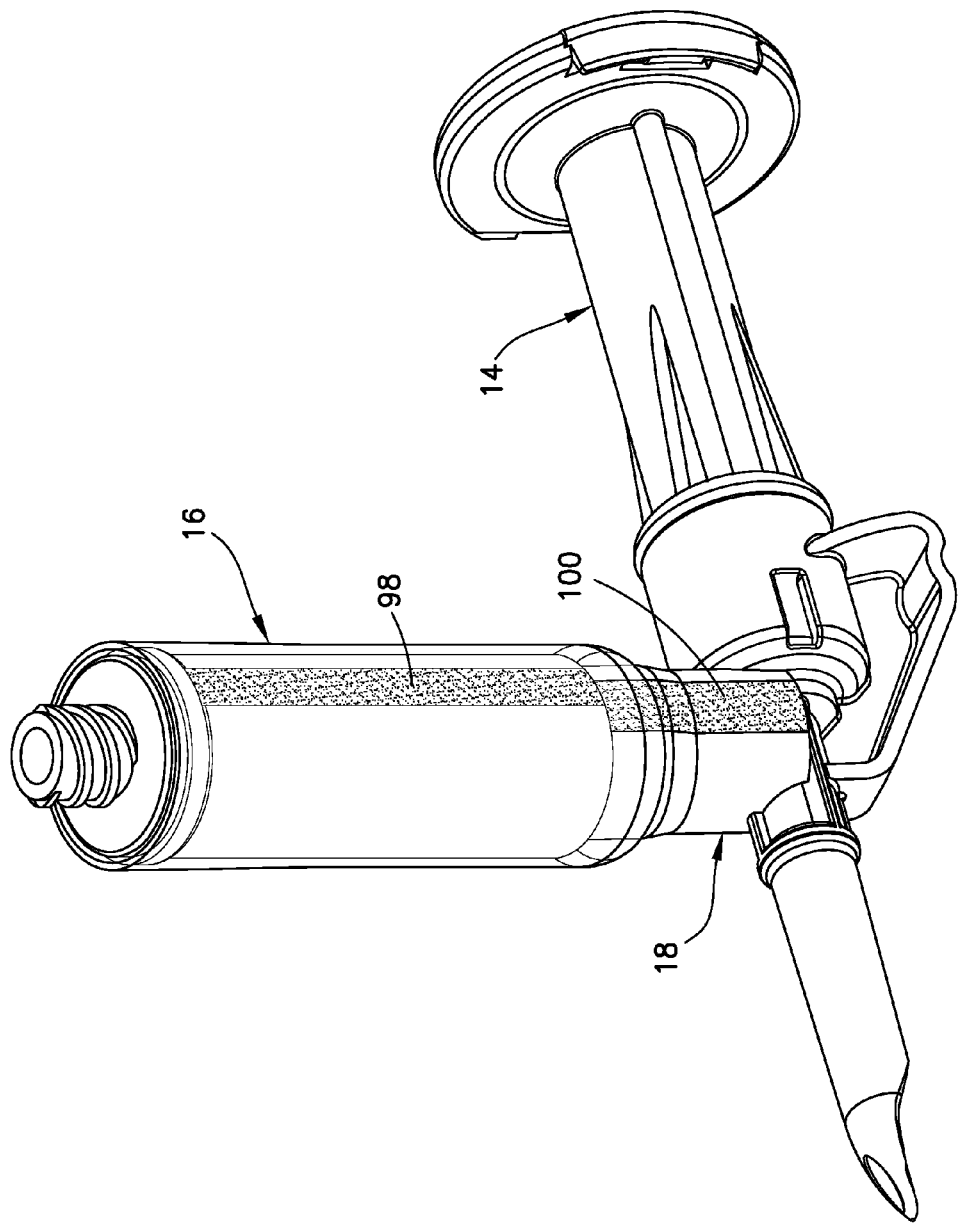
FIG. 13 is a perspective view of a medical connector system according to one aspect of the present invention, showing the first connector of FIG. 8 locked with the second connector of FIG. 10.
Figure 16:
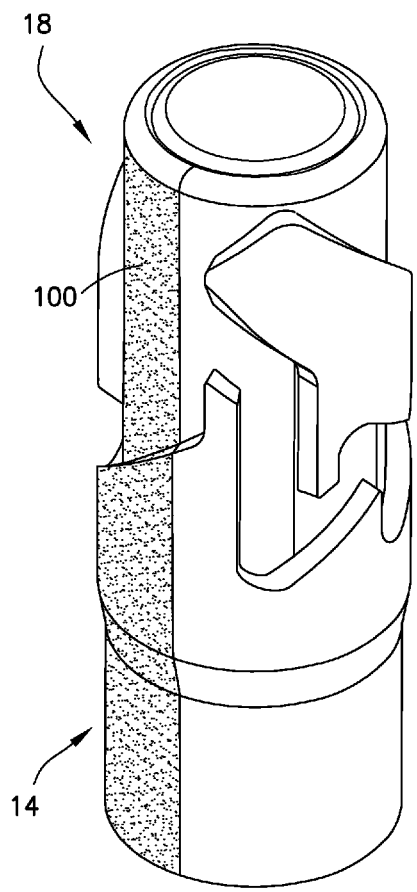
FIG. 16 is a top perspective view of a second connector of a medical connector system shown according to another aspect of the present invention, showing the connector with an indicator band in conjunction with a patient connector.
Figure 17:
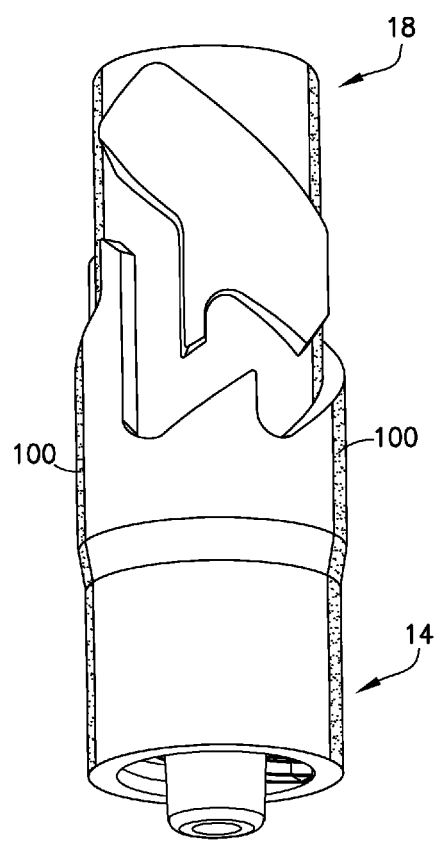
FIG. 17 is a bottom perspective view of the second connector of FIG. 16 according to one aspect of the present invention.
Figure 20:
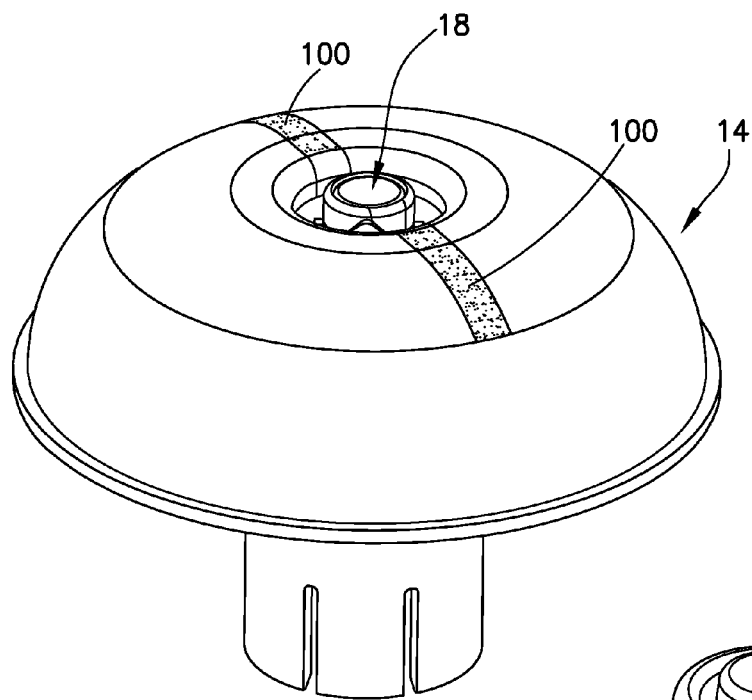
FIG. 20 is a perspective view of a second connector of a medical connector system shown according to yet another aspect of the present invention, showing the connector with an indicator band in conjunction with a vial adapter.
Figure 21:
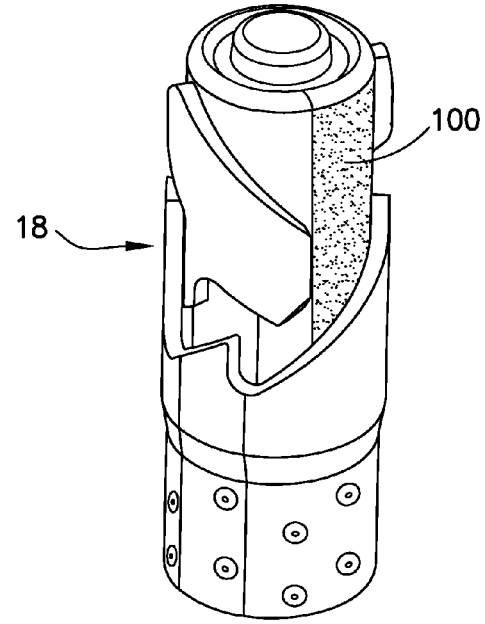
FIG. 21 is a perspective view of a second connector of a medical connector system shown according to yet another aspect of the present invention, showing the connector with an indicator band in conjunction with a patient connector.
Figures 22, 23:
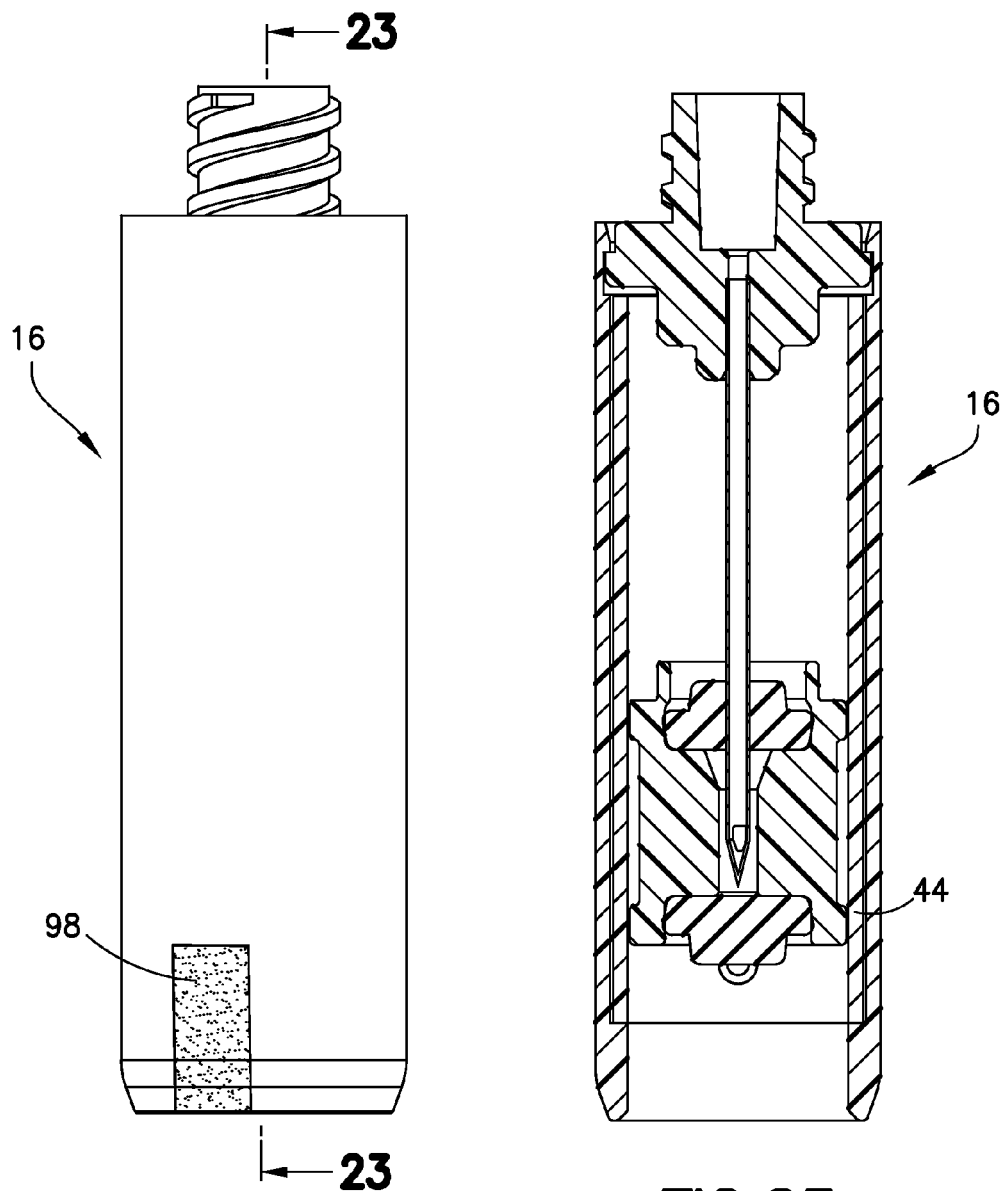
FIG. 22 is a perspective view of a first connector of a medical connector system shown according to a further aspect of the present invention, showing the connector with an opaque housing and indicator band.
FIG. 23 is a cross-sectional view of the first connector of FIG. 22 taken along line 23-23 in FIG. 22.
Figure 24:
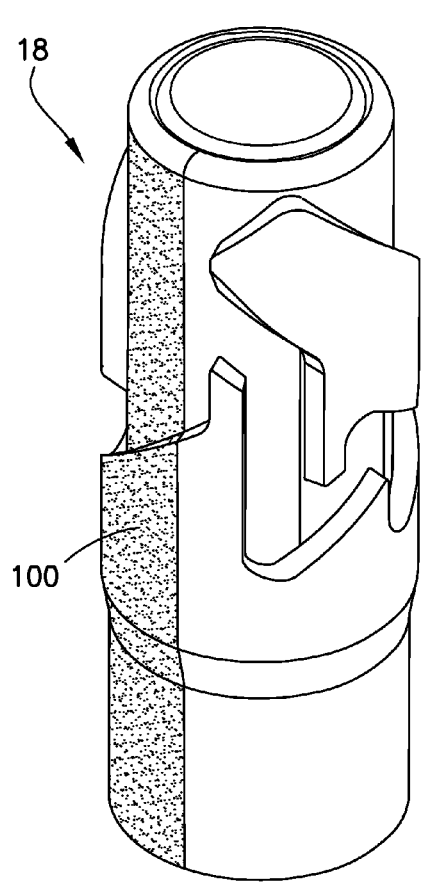
FIG. 24 is a perspective view of a second connector of a medical connector system shown according to a further aspect of the present invention, showing the connector with an indicator band in conjunction with a patient connector.
Figure 25:
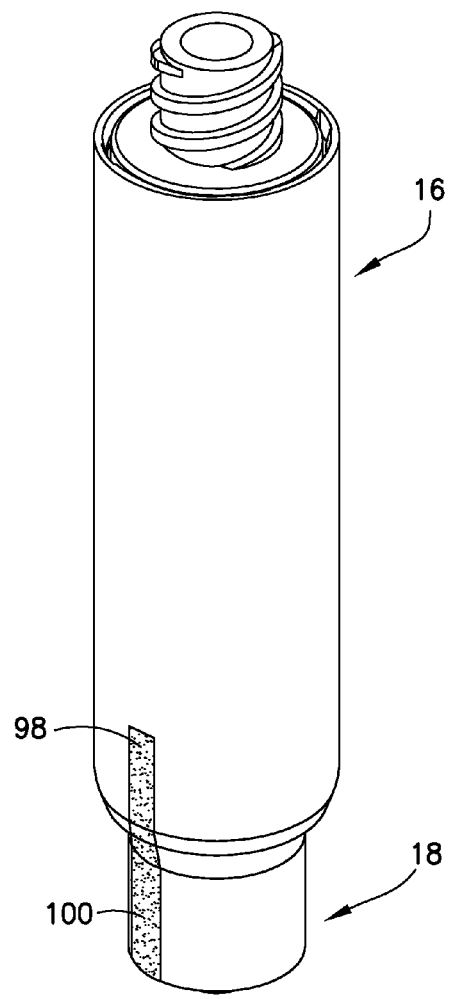
FIG. 25 is a perspective view of a medical connector system according to one aspect of the present invention, showing the first connector of FIG. 22 locked with the second connector of FIG. 24.

The indicator line 98 may extend the full length of the cam member 44 and the second connector 18 as shown in FIGS. 8 and 11 or may only extend for part of the length of the cam member 44 and the second connector 18 as shown in FIG. 19.

Alternatively, if the cam member 44 is external from the housing 20, the housing 20 need not be transparent.

Figure 26:
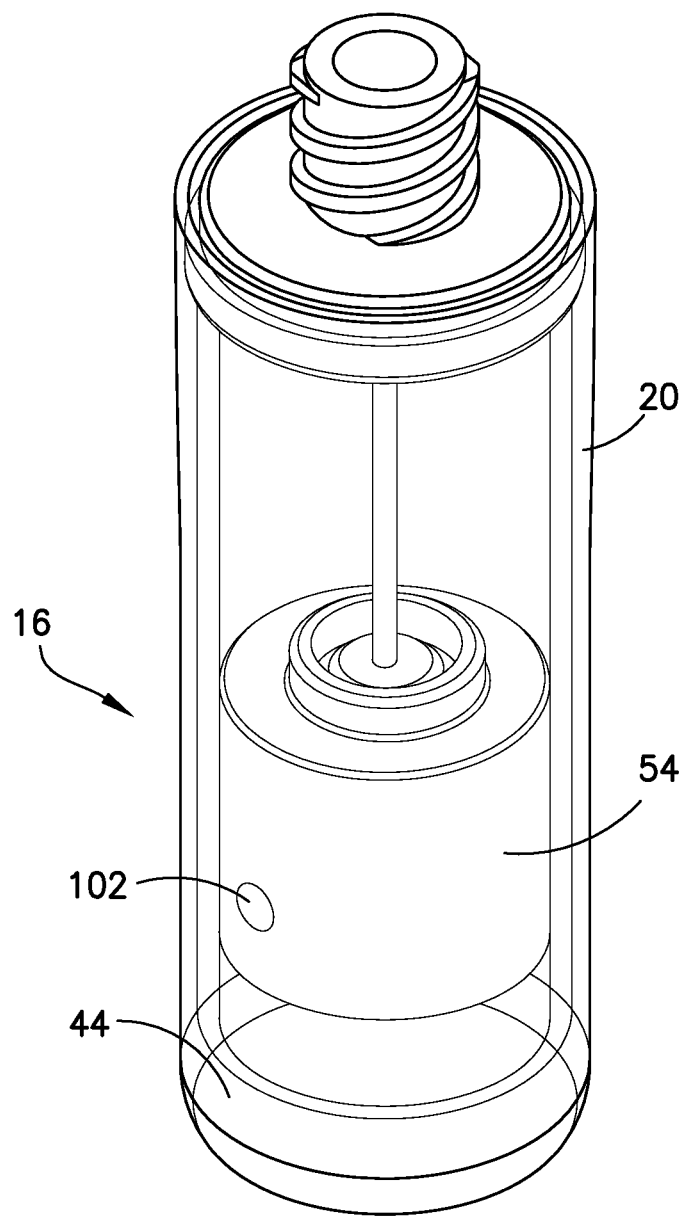
FIG. 26 is a perspective view of a first connector of a medical connector system shown according to another aspect of the present invention, showing the connector with a transparent housing and an indicator.
Figure 27:
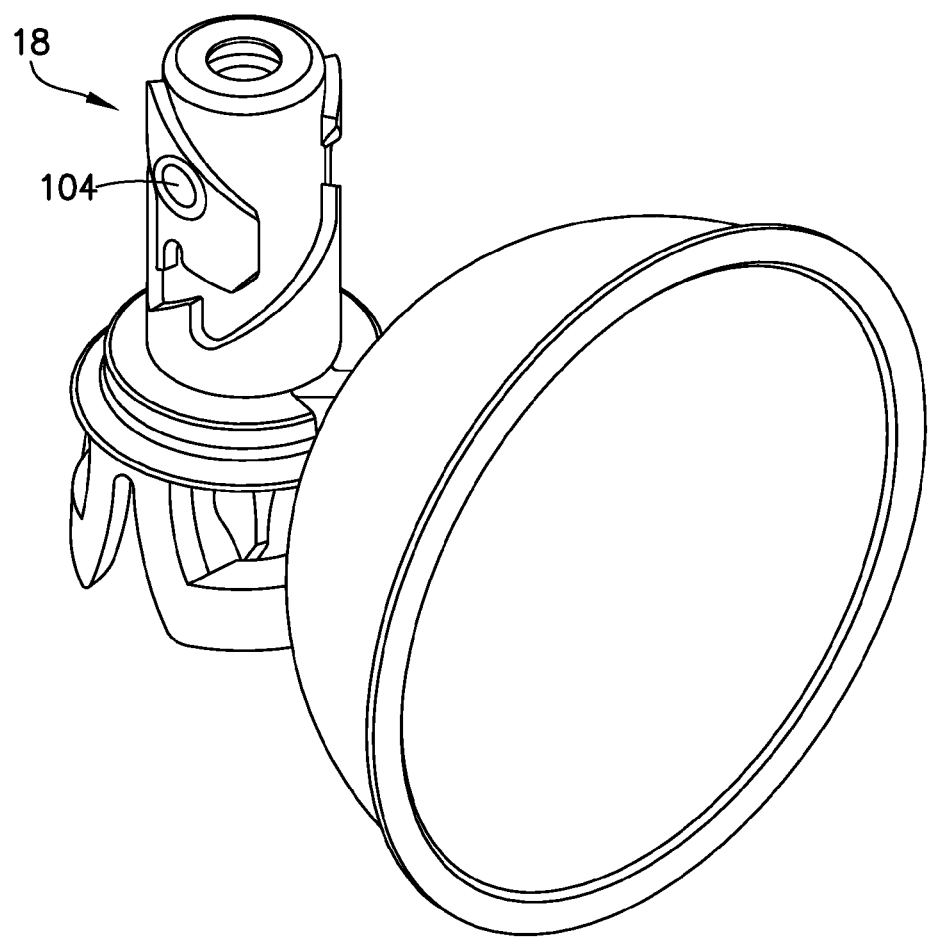
FIG. 27 is a perspective view of a second connector of a medical connector system shown according to another aspect of the present invention, showing the connector with an indicator.
Figure 28:
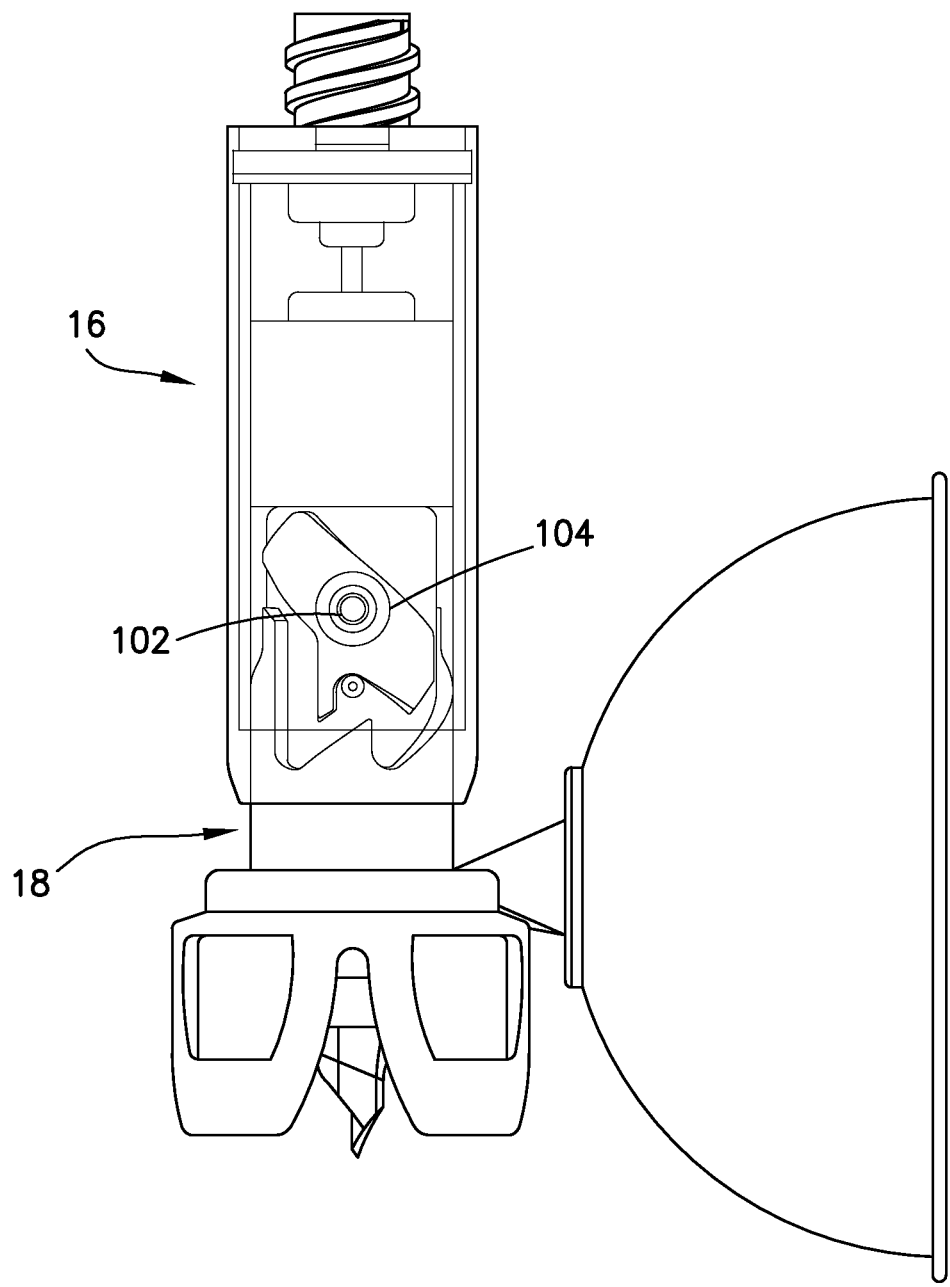
FIG. 28 is a perspective view of a medical connector system according to one aspect of the present invention, showing the first connector of FIG. 26 locked with the second connector of FIG. 27.
Figure 29:
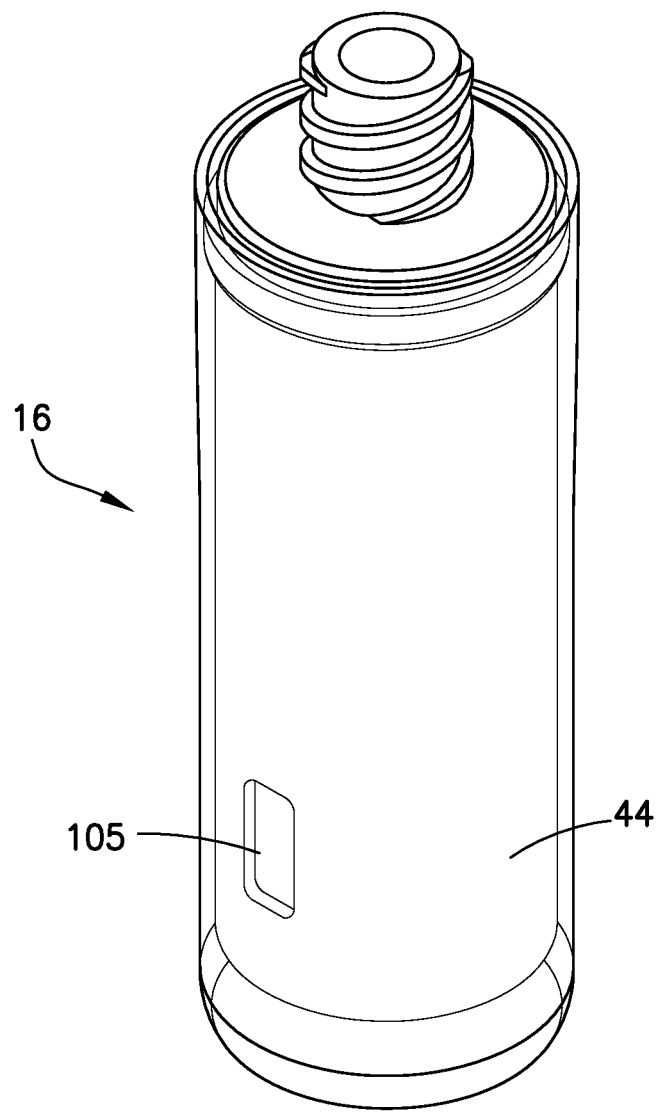
FIG. 29 is a perspective view of a first connector of a medical connector system shown according to yet another aspect of the present invention, showing the connector with a transparent housing and a window.
Figure 30:
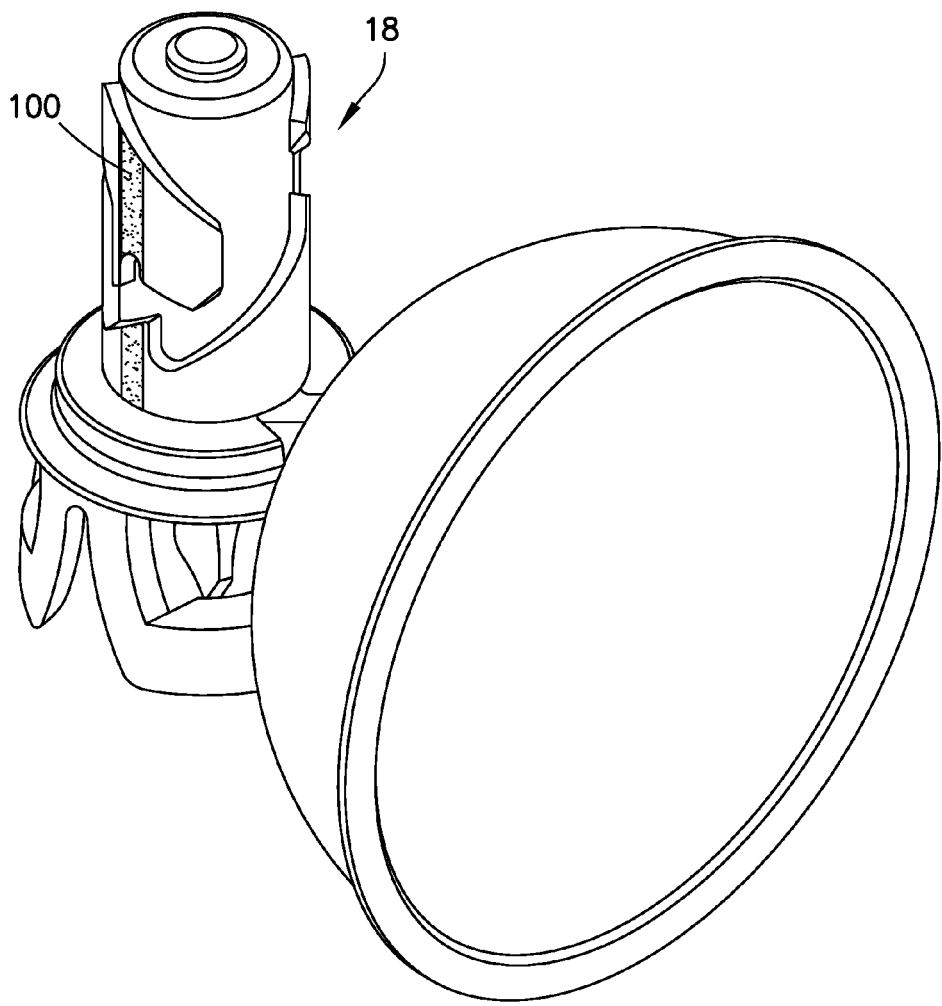
FIG. 30 is a perspective view of a second connector of a medical connector system shown according to yet another aspect of the present invention, showing the connector with an indicator band.
Figure 31:
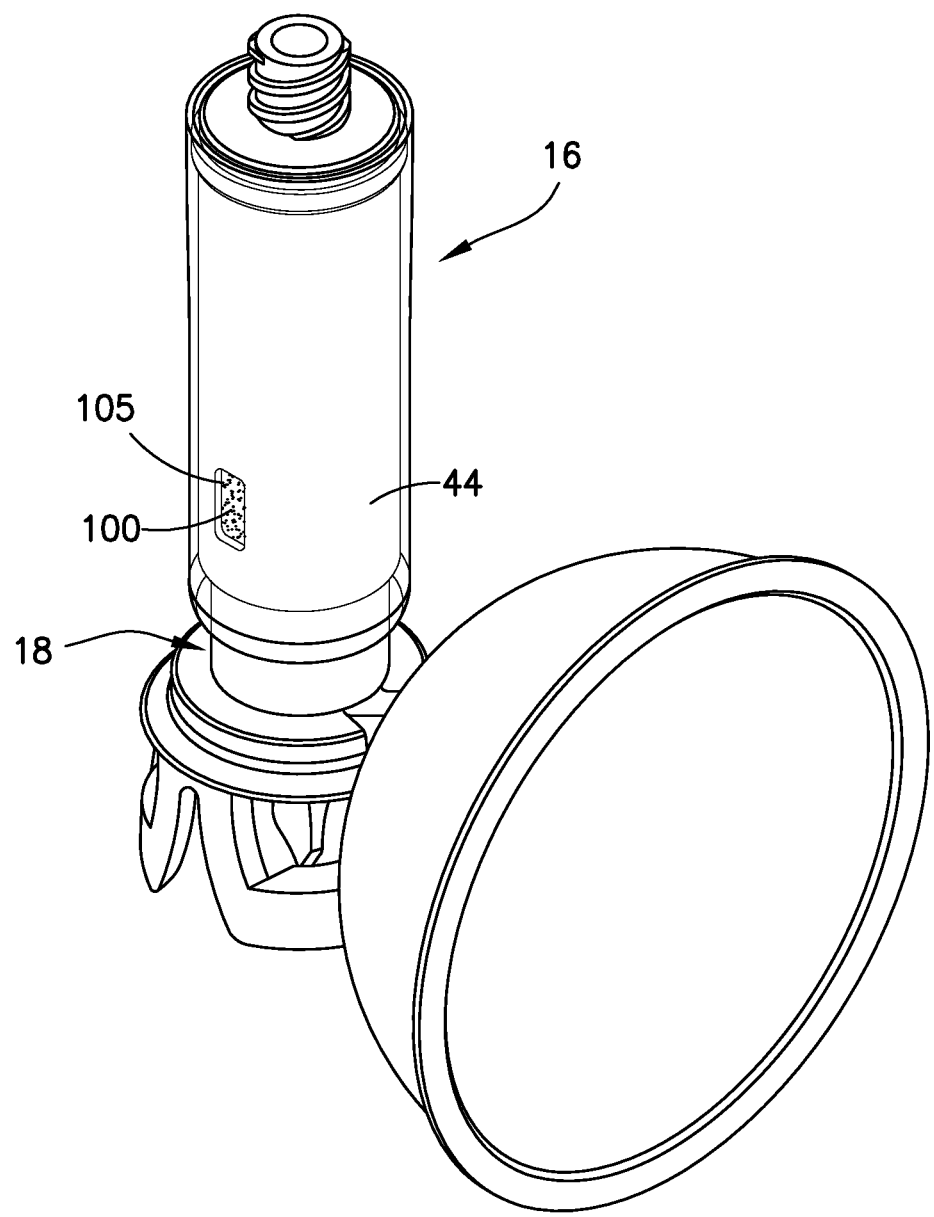
FIG. 31 is a perspective view of a medical connector system according to one aspect of the present invention, showing the first connector of FIG. 29 locked with the second connector of FIG. 30.
Figure 32:
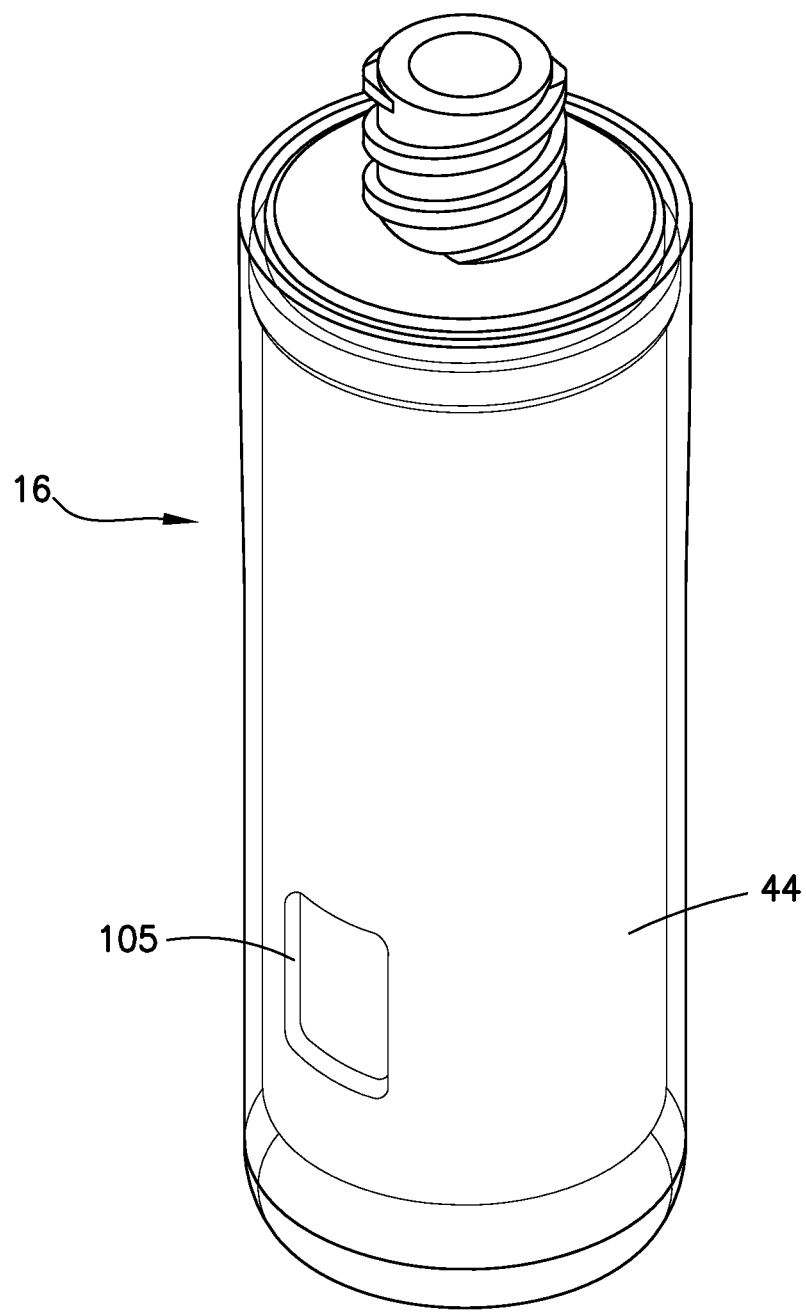
FIG. 32 is a perspective view of a first connector of a medical connector system shown according to a further aspect of the present invention, showing the connector with a transparent housing and a window.

In another aspect, shown in FIGS. 26-28, with a connector system having a cam member 44, the first connector 16 may have a dot 102 on the outer surface of the housing 20. In this case, the housing 20 of the first connector 16 is transparent. The second connector 18 may have a circle 104. When the first connector 16 is in locking engagement with the second connector 18, the dot 104 on the housing 102 will be visible through the transparent housing 20 and will be located in the circle 104 on the second connector 18 to give a visual indication to the user that the connector system is locked.

Figure 33:
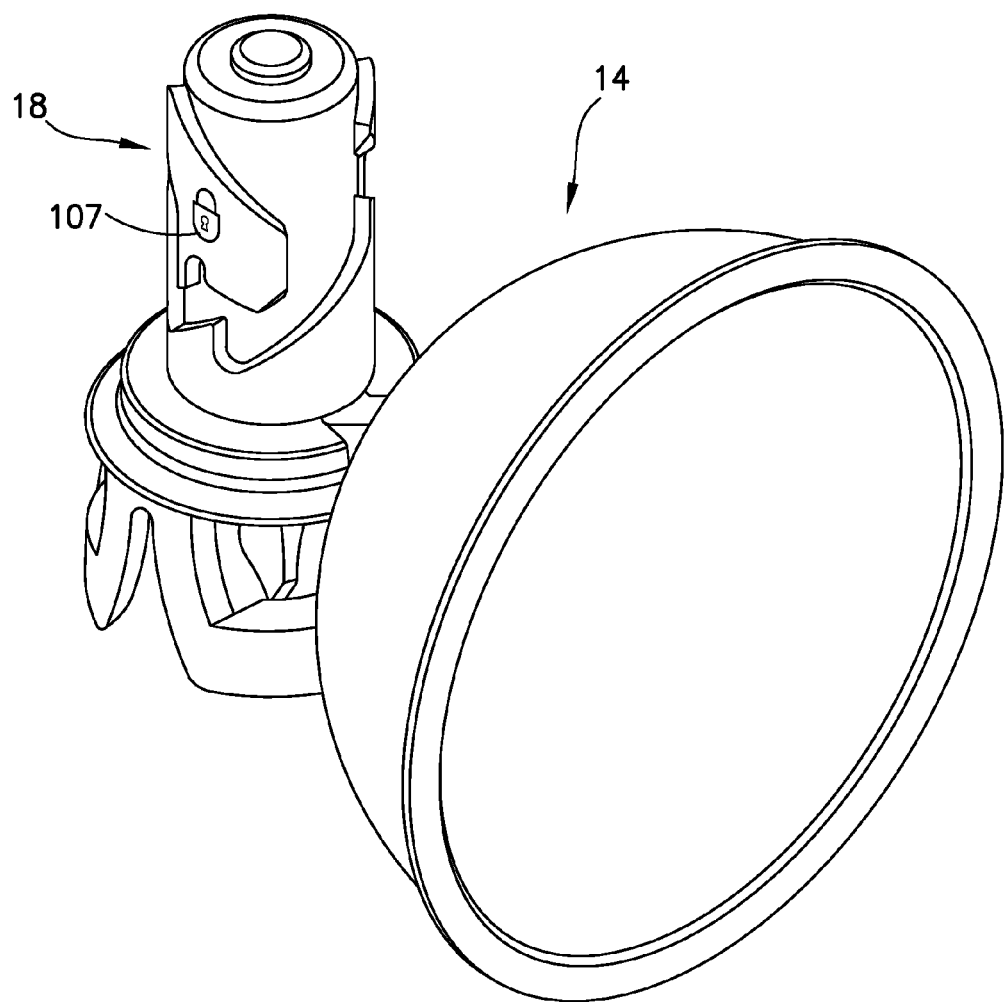
FIG. 33 is a perspective view of a second connector of a medical connector system shown according to a further aspect of the present invention, showing the connector with an indicator mark.
Figure 34:
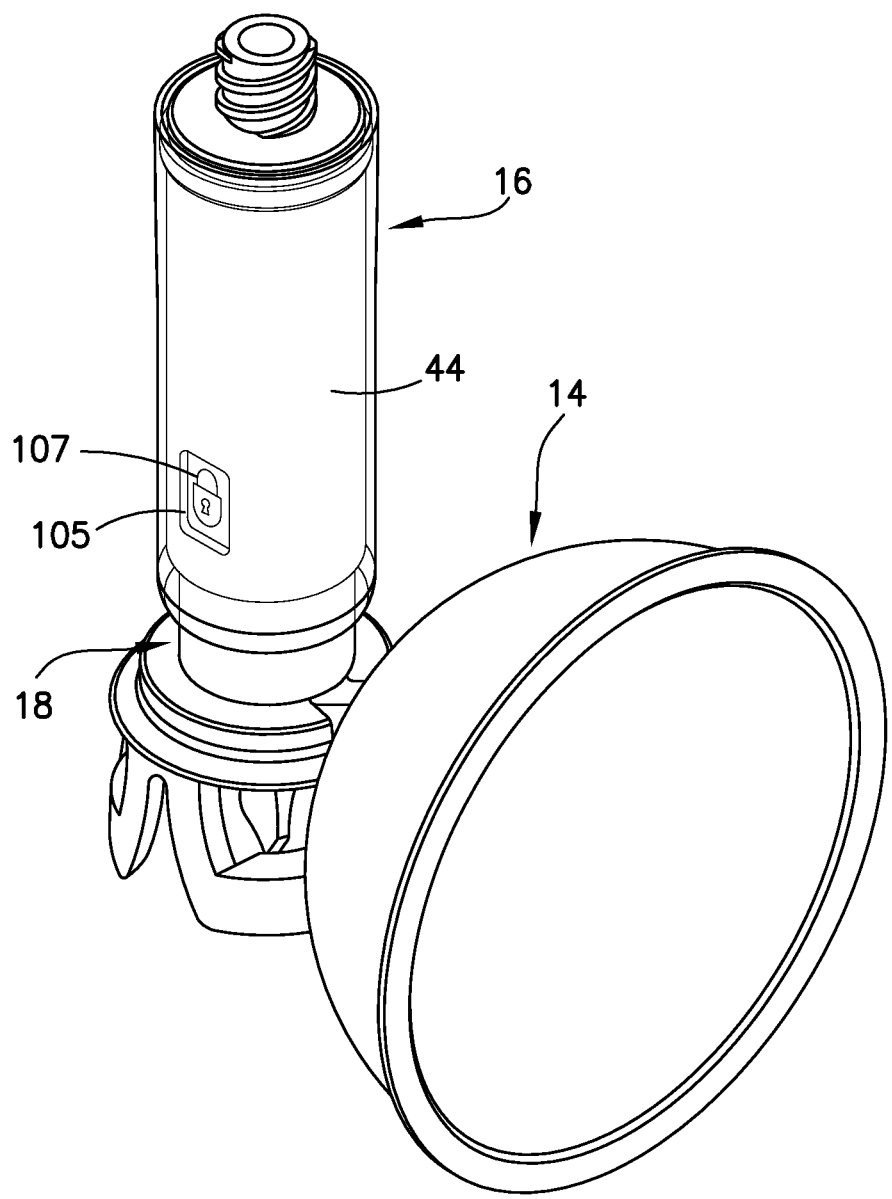
FIG. 34 is a perspective view of a/medical connector system according to one aspect of the present invention, showing the first connector of FIG. 32 locked with the second connector of FIG. 33.

In another aspect, shown in FIGS. 29-34, with a connector system having a cam member 44, the cam member 44 may include a window 105 and the second connector may include an indicator band 100 (FIGS. 30 and 31) or an indicator mark 107 (FIGS. 33 and 34). In this case, the housing 20 of the first connector 16 is transparent. When the first connector 16 is in locking engagement with the second connector 18, the indicator band 100 or indicator mark 107 will be visible through the transparent housing 20 and will be located in the window 105 of the cam member 44 to give a visual indication to the user that the connector system is locked. In yet another aspect, instead of the indicator band 100 or indicator mark 107 being on the second connector 18, the colored portion may be provided on the carrier 54. In this case, the indicator could be visible through a window in the opaque housing when the carrier 54 is moved within the housing 20.

Referring to FIGS. 35-38, although the housing 20 of the first connector 16 is shown to be generally cylindrical in FIG. 2, for example, the housing 20 of the first connector 16 may also include features to enhance the ability of a user to grip the housing 20.

Figure 35:
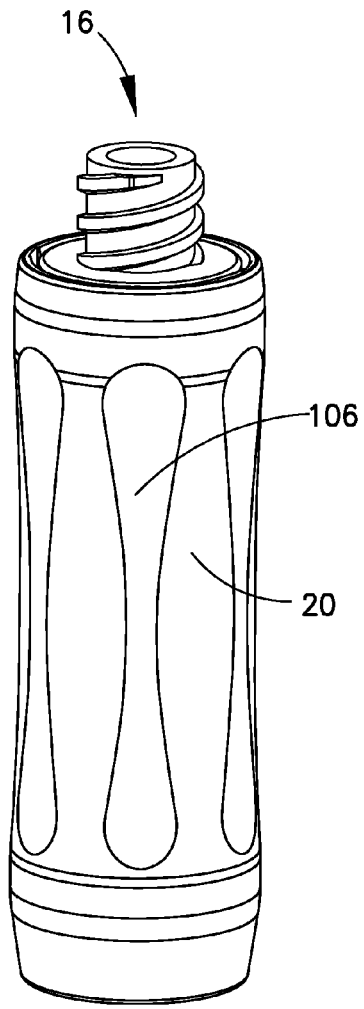
FIG. 35 is a perspective view of the first connector of medical connector system of FIG. 1, showing a grip configuration according to an alternative aspect of the present invention.
Figure 36:
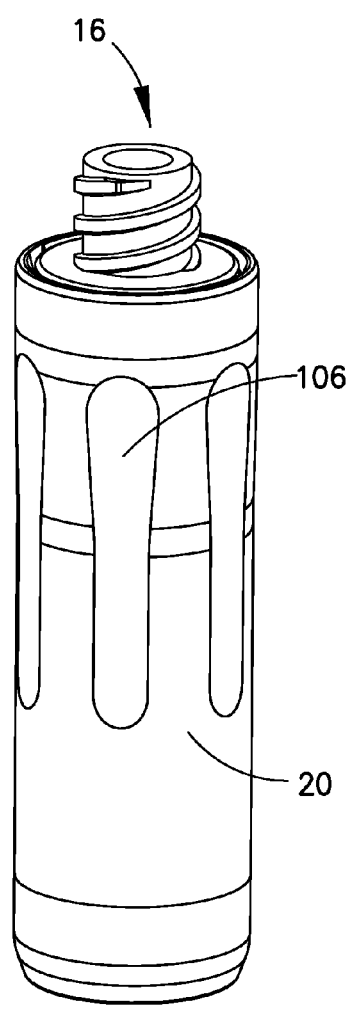
FIG. 36 is a perspective view of the first connector of medical connector system of FIG. 1, showing a grip configuration according to a second alternative aspect of the present invention.

Referring to FIGS. 35 and 36, the housing 20 of the first connector 16 may include grip portions 106 that are generally planar regions compared to the cylindrical surface of the remaining portion of the housing 20. The housing 20 is generally cylindrical in FIG. 35 with a recessed, planar grip portion 106 that has an hourglass-shaped circumference. The housing is generally cylindrical in FIG. 36 with a recessed, planar grip portion 106 that has a generally rectangle-shaped circumference with rounded ends. The grip portions 106 provide a contact surface to allow the housing 20 to be more readily gripped by a user of the connector 16.

Figure 37:
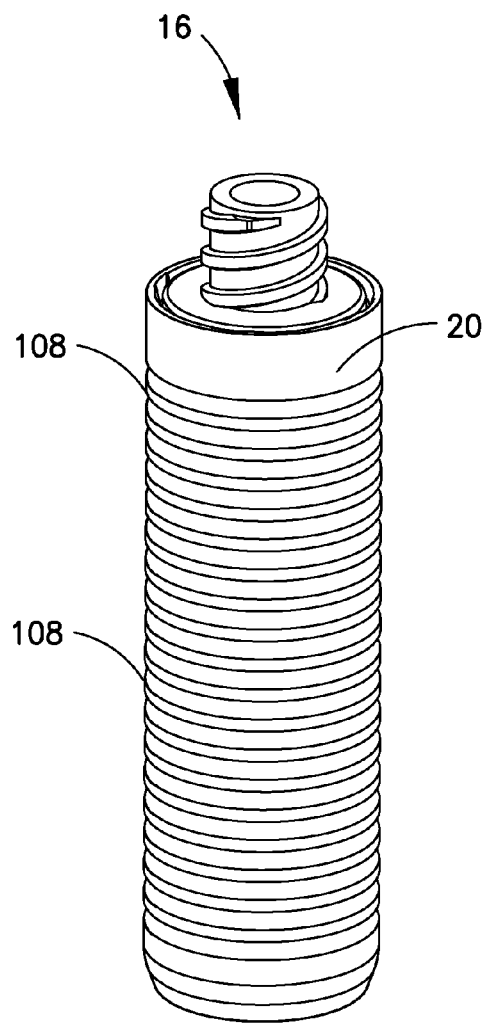
FIG. 37 is a perspective view of the first connector of medical connector system of FIG. 1, showing a grip configuration according to third alternative aspect of the present invention.

Referring to FIG. 37, the housing 20 of the first connector 16 may include a plurality of annular ribs 108 that extend circumferentially around the outer surface of the housing 20. The housing 20 may include a plurality of the annular ribs 108 that extend the full length or only a portion of the length of the housing 20. The annular ribs 108 provide a surface for a user to more readily grip the connector 16.

Figure 38:
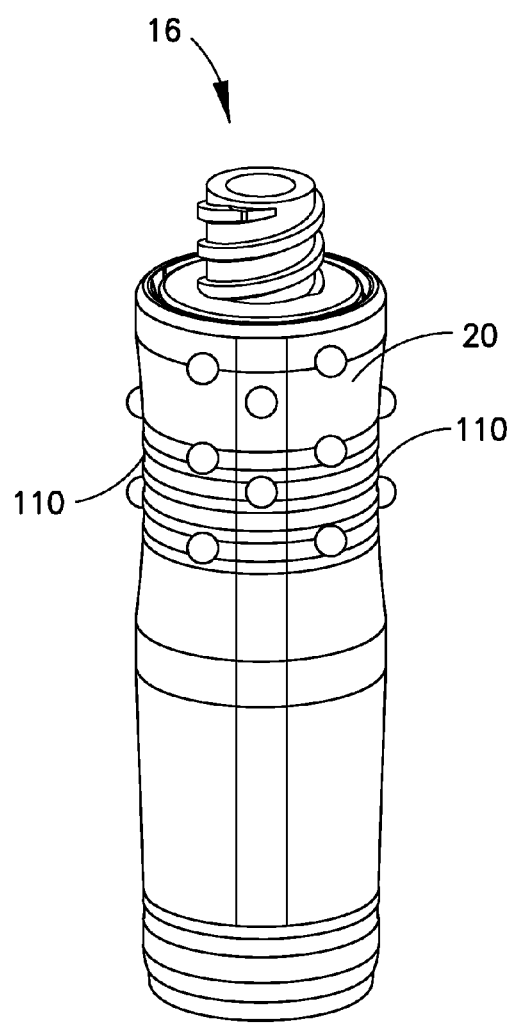
FIG. 38 is a perspective view of the first connector of medical connector system of FIG. 1, showing a grip configuration according to a fourth alternative aspect of the present invention.
Figure 39:
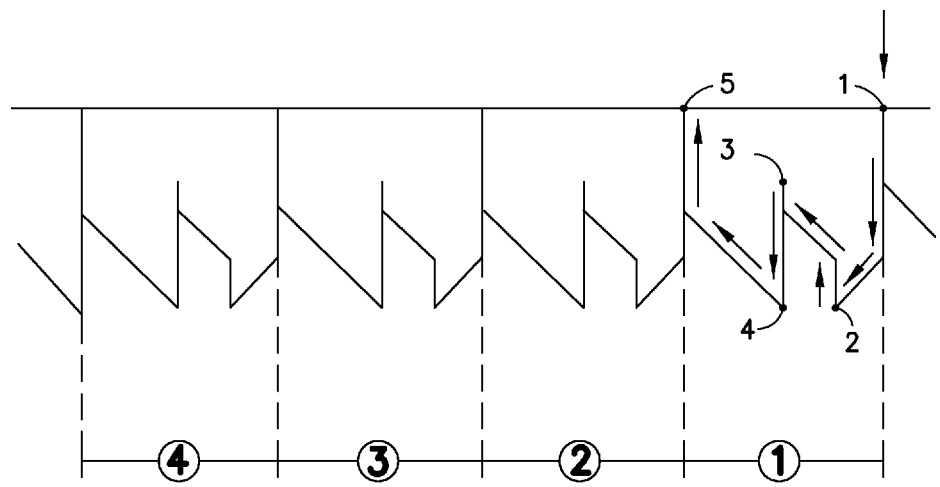
FIG. 39 is a schematic of a groove of the second connector according to a first alternative aspect.
Figure 40:
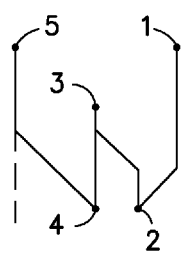
FIG. 40 is a schematic of a groove of the second connector according to a second alternative aspect.
Figure 41:
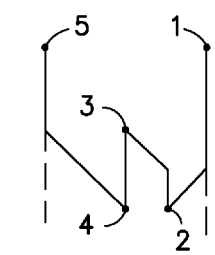
FIG. 41 is a schematic of a groove of the second connector according to a third alternative aspect.
Figure 42:
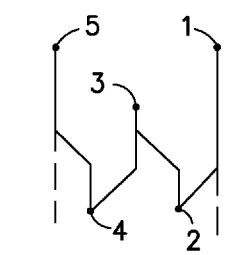
FIG. 42 is a schematic of a groove of the second connector according to a fourth alternative aspect.
Figure 43:
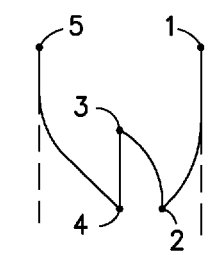
FIG. 43 is a schematic of a groove of the second connector according to a fifth alternative aspect.

Referring to FIG. 38, the housing 20 of the first connector 16 may also define a concave grip portion 110 including nubs or projections. The concave grip portion 110 is a portion of the housing 20 that extends radially inwardly around the circumference of the housing 20 to provide a contact surface that allows the connector 16 to be more readily gripped by a user.

Although the projection 46 of the first connector 16 extends radially inward and the groove 76 of the second connector 18 is positioned on the outer surface of the second connector 18, the projection 46 may extend radially outward and provided on the outer surface of the second connector 18 with the groove 76 of the second connector 18 provided on an interior surface of the second connector 18.

Figure 44:
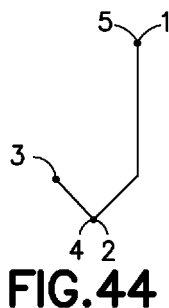
FIG. 44 is a schematic of a groove of the second connector according to a sixth alternative aspect.
Figure 45:
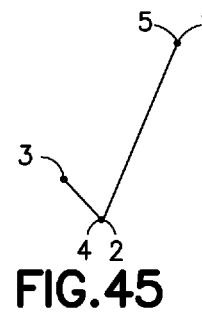
FIG. 45 is a schematic of a groove of the second connector according to a seventh alternative aspect.
Figure 46:
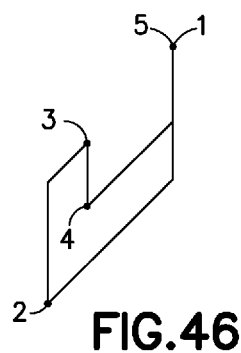
FIG. 46 is a schematic of a groove of the second connector according to an eighth alternative aspect.

As shown in FIGS. 39-46, the groove 76 of the second connector 18 can take any of a number of paths as long as, upon application and release of a first set of opposing axial forces applied to the proximal end 77 of the first connector 16 and the distal end 70 of the second connector 18, the first connector 16 is locked to the second connector 18 and, upon application and release of a second set of opposing axial forces to the proximal end 77 of the first connector 16 and the distal end 70 of the second connector 18, the first connector 16 is released from the second connector 18. These include: pathways that can be linked and repeated (FIG. 39), pathways that follow the same trail during application and release of the first set of opposing axial forces and application and release of the second set of axial forces (FIGS. 44 and 45), pathways that have curved sections (FIG. 43), and pathways that are looped such that they have a common entry and exit point but follow a loop through the majority of the locking and releasing steps (FIG. 46). All paths may include at least five positions: (1) a starting position, (2) an initial base position, (3) an intermediate (or locked) position, (4) a secondary base position, and (5) an ending position. For some paths, the initial base position (2) and the secondary base position (4) are the same (FIGS. 44 and 45). Similarly, the starting position (1) and the ending position (5) may also be the same depending on the path (FIG. 46). While the aspects shown in the figures have two projections 46 on the cam member 44 and two grooves 76 on the second connector 18, any number of projections 46 may be used. The corresponding groove or grooves 76 may be altered or scaled to account for the number and/or position of the projections 46 as long as the shape of the groove 76 allows for locking of the first connector 16 to the second connector 18 upon application and release of a first set of opposing axial forces and release of the first connector 16 from the second connector 18 upon application and release of a second set of opposing axial forces. In addition, the number of projections 46 and grooves 76 need not be equal. For example, one projection 46 could be used with two or more repeated groove 76 patterns or two projections 46 could be used with four repeated groove 76 patterns.

The connector system has been previously described as having a cam member 44 with at least one protrusion 46 that is rotatably disposed in the housing 20 of the first connector 16 with the second connector 18 being stationary. Alternatively, the protrusion 46 may be fixed directly to the housing 20 or keyed to the housing 20. In this case, the second connector 18 would then be placed on a secondary component (similar to a cylinder) allowing the groove 76 to rotate relative to the housing 20 and the protrusion 46.

The connector system has also been previously described as having the groove 76 on the exterior of the second connector 18 and the cam member 44 as part of the first connector 16. Alternatively, the groove 76 could be placed on the inner wall of the housing 20 of the first connector 16 and the cam member 44 could be placed on the exterior of the second connector 18. There are two variations of this aspect. First, the cam member 44 with at least one protrusion 46 could be a rotating washer on the exterior of the second connector 18 and the groove 76 could be fixed in the inner wall of the housing 20 of the first connector 16. Second, the protrusion 46 could be fixed to the exterior of the second connector 18 and the groove could be placed on the inside of a secondary component (like a cylinder) that could rotate freely within the inner walls of the housing 20 of the first connector 16 allowing the groove 76 to rotate with respect to the protrusion 46.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

The invention claimed is:

1. A medical connector system comprising:
a first connector having a proximal end and a distal end, the first connector comprising a housing defining a central opening that receives a carrier member, a biasing member, a needle cannula, and a cam member, the biasing member engaging and biasing the carrier member towards the distal end of the first connector, the cam member having at least one projection extending into the central opening of the housing of the first connector with the cam member being rotatable relative to the housing of the first connector, the carrier member having at least one sealing member; and
a second connector having an outer surface, a proximal end, and a distal end, the outer surface of the second connector comprising at least one groove for receiving the at least one projection,
wherein the proximal end of the second connector is configured to be at least partially disposed within a distal end of the housing of the first connector, and
wherein upon application and release of a first set of opposing axial forces applied to the proximal end of the first connector and the distal end of the second connector, the first connector is locked to the second connector with the at least one projection engaged with that at least one groove and the needle cannula extending through the at least one sealing member and, upon application and release of a second set of opposing axial forces to the proximal end of the first connector and the distal end of the second connector, the first connector is released from the second connector with the at least one projection released from engagement with the at least one groove.

2. The medical connector system according to claim 1, wherein upon application and release of the first set of opposing axial forces applied to the proximal end of the first connector and the distal end of the second connector, the biasing member biases the first connector in a proximal direction with respect to the second connector such that the at least one projection of the first connector engages the at least one groove of the second connector and locks the first connector onto the second connector.

3. The medical connector system according to claim 2, wherein upon application and release of the second set of opposing axial forces to the proximal end of the first connector and the distal end of the second connector, the biasing member biases the first connector in a proximal direction with respect to the second connector releasing the engagement between the at least one projection of the first connector and the at least one groove of the second connector.

4. The medical connector system according to claim 1, wherein the at least one groove comprises:
a first section extending axially in a distal direction;
a second section extending from a distal end of the first section and sloping in a distal direction away from the distal end of the first section;
a third section extending axially in a proximal direction from a distal end of the second section;
a fourth section extending from a proximal end of the third section and sloping in a proximal direction away from the proximal end of the third section;
a fifth section extending axially in a distal direction from a proximal end of the fourth section;
a sixth section extending from a distal end of the fifth section and sloping in a distal direction away from the distal end of the fifth section;
a seventh section extending axially in a proximal direction from a distal end of the sixth section; and
an eighth section extending from a proximal end of the seventh section and sloping in a proximal direction away from the proximal end of the seventh section.

5. The medical connector system according to claim 4, wherein the at least one groove further comprises an additional section extending axially in a proximal direction from the proximal end of the fourth section and the fifth section extends from a distal end of the additional section.

6. The medical connector system according to claim 5, wherein the first connector is locked to the second connector when the at least one projection on the first connector is disposed within a proximal end of the additional section of the at least one groove of the second connector.

7. The medical connector system according to claim 4, wherein the second connector further comprises a distally sloping ledge on an exterior surface extending to a proximal end of the first section of the at least one groove.

8. The medical connector system according to claim 4, wherein the first connector is locked to the second connector when the at least one projection of the first connector is disposed within the proximal end of the fourth section of the at least one groove of the second connector.

9. The medical connector system according to claim 4, wherein upon application of the first set of opposing axial forces to the proximal end of the first connector and the distal end of the second connector, the at least one projection travels through the first and second sections of the at least one groove of the second connector.

10. The medical connector system according to claim 4, wherein upon release of the first set of opposing axial forces to the proximal end of the first connector and the distal end of the second connector, the biasing member biases the first connector in a proximal direction with respect to the second connector such that the at least one projection travels through the third and fourth sections of the at least one groove of the second connector and is disposed within the proximal end of the fourth section of the second connector.

11. The medical connector system according to claim 4, wherein upon application of the second set of opposing axial forces to the proximal end of the first connector and the distal end of the second connector, the at least one projection travels through the fifth and sixth sections of the at least one groove of the second connector.

12. The medical connector system according to claim 4, wherein upon release of the second set of opposing axial forces to the proximal end of the first connector and the distal end of the second connector, the biasing member biases the first connector in a proximal direction with respect to the second connector such that the at least one projection travels through the seventh and eighth sections of the at least one groove of the second connector releasing engagement between the at least one projection and the at least one groove of the second connector.

13. The medical connector of claim 1, wherein the first connector comprises a first indicator and the second connector comprises a second indicator, and wherein upon application and release of the first set of opposing axial forces applied to the proximal end of the first connector and the distal end of the second connector, the first connector is locked relative to the second connector in an axial direction and the first indicator is aligned with the second indicator.

14. The medical connector system of claim 13, wherein the first indicator and the second indicator are axial bands.

15. The medical connector system of claim 13, wherein the first indicator is a dot and the second indicator is a circle.

16. A method of transferring a fluid from a first medical device used for receiving or dispensing fluids to a second medical device used for receiving or dispensing fluids comprising:

provptroviding a first connector having a proximal end and a distal end, wherein the proximal end is connected to the first medical device and the distal end is open, the first connector comprising a housing and a needle cannula;

providing a second connector having a proximal end and a distal end, wherein the distal end is connected to the second medical device, the second connector comprising a central passageway extending from the proximal end to the distal end;

inserting the proximal end of the second connector at least partially into the open distal end of the first connector;

applying and releasing a first set of opposing axial forces to the proximal end of the first connector and the distal end of the second connector, wherein the first connector is locked to the second connector upon release of the first set of opposing axial forces and the needle cannula extends into the central passageway beyond the distal end of the second connector and into the second medical device; and transferring the fluid from the first medical device to the second medical device through the needle cannula.

17. The method of claim 16 further comprising:

applying and releasing a second set of opposing axial forces to the proximal end of the first connector and the distal end of the second connector, wherein the first connector is released from the locking engagement with the second connector and the needle cannula is disposed within the housing of the first connector upon release of the second set of opposing axial forces.

\* \* \* \* \*